US010856783B2

(12) United States Patent
Ajima

(10) Patent No.: US 10,856,783 B2
(45) Date of Patent: Dec. 8, 2020

(54) ELECTRONIC DEVICE AND SYSTEM

(71) Applicant: KYOCERA Corporation, Kyoto (JP)

(72) Inventor: Hiromi Ajima, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 434 days.

(21) Appl. No.: 15/568,319

(22) PCT Filed: Apr. 14, 2016

(86) PCT No.: PCT/JP2016/002026

§ 371 (c)(1),
(2) Date: Oct. 20, 2017

(87) PCT Pub. No.: WO2016/174839

PCT Pub. Date: Nov. 3, 2016

(65) Prior Publication Data

US 2018/0116571 A1 May 3, 2018

(30) Foreign Application Priority Data

Apr. 28, 2015 (JP) ................................ 2015-091577

(51) Int. Cl.

| | |
|---|---|
| ***A61B 5/145*** | (2006.01) |
| ***A61B 5/00*** | (2006.01) |
| ***A61B 5/02*** | (2006.01) |
| ***A61B 5/026*** | (2006.01) |
| ***A61B 5/024*** | (2006.01) |

(Continued)

(52) U.S. Cl.

CPC ............ *A61B 5/14532* (2013.01); *A61B 5/00* (2013.01); *A61B 5/02* (2013.01); *A61B 5/024* (2013.01); *A61B 5/026* (2013.01); *A61B 5/1455* (2013.01); *A61B 5/021* (2013.01)

(58) Field of Classification Search

CPC ....... A61B 5/145; A61B 5/024; A61B 5/1455; A61B 5/00; A61B 5/02; A61B 5/026; A61B 5/14532; A61B 5/021

See application file for complete search history.

(56) References Cited

U.S. PATENT DOCUMENTS

| | | | |
|---|---|---|---|
| 8,251,910 | B2 | 8/2012 | Saito et al. |
| 2002/0188210 | A1 | 12/2002 | Aizawa |
| 2008/0275317 | A1 | 11/2008 | Cho et al. |

(Continued)

FOREIGN PATENT DOCUMENTS

| | | | |
|---|---|---|---|
| CN | 101495033 | A | 7/2009 |
| EP | 2047793 | A1 | 4/2009 |

(Continued)

OTHER PUBLICATIONS

Choi, et al. "The Association of Brachial-Ankle Pulse Wave Velocity with 30-Minute Post-Challenge Plasma Glucose Levels in Korean Adults with No History of Type 2 Diabetes," Korean Diabetes J 2010;34:287-293 (Year: 2008).*

(Continued)

*Primary Examiner* — Eric J Messersmith

(74) *Attorney, Agent, or Firm* — Studebaker & Brackett PC

(57) ABSTRACT

An electronic device includes a sensor that acquires a pulse wave and a controller that calculates an index based on the acquired pulse wave. The controller estimates the subject's state of glucose metabolism or lipid metabolism using the calculated index.

12 Claims, 18 Drawing Sheets

$$AI_n = (P_{Rn} - P_{Sn}) / (P_{Fn} - P_{Sn})$$

(51) Int. Cl.

| | |
|---|---|
| ***A61B 5/1455*** | (2006.01) |
| *A61B 5/021* | (2006.01) |

(56) References Cited

U.S. PATENT DOCUMENTS

| | | | | |
|---|---|---|---|---|
| 2009/0306523 | A1 | 12/2009 | Saito et al. | |
| 2010/0222652 | A1 | 9/2010 | Cho et al. | |
| 2012/0059237 | A1 * | 3/2012 | Amir .................... | A61B 5/0285 600/365 |
| 2016/0213296 | A1 | 7/2016 | Kikuchi et al. | |

FOREIGN PATENT DOCUMENTS

| | | | |
|---|---|---|---|
| JP | H07-37104 | U | 7/1995 |
| JP | 2002-360530 | A | 12/2002 |
| JP | 2008-183256 | A | 8/2008 |
| JP | 2010-537751 | A | 12/2010 |
| KR | 2009-0127517 | A | 12/2009 |
| WO | 2015/037281 | A1 | 3/2015 |

OTHER PUBLICATIONS

International Search Report issued in PCT/JP2016/002026; dated Jul. 5, 2016.

Written Opinion issued in PCT/JP2016/002026; dated Jul. 5, 2016.

Makoto Sato et al.; "Behavior Recognition Using Biological Data and Acceleration Data"; 65th Information Process Conference (in 2003); a collection of lecture papers of national convention (5); Mar. 25, 2003, pp. 5-239-5-242.

Jerry R. Greenfield et al., Effect of postprandial insulinemia and insulin resistance on measurement of arterial stiffness (augmentation index), International Journal of Cardiology, 2007, pp. 50-56, Elsevier.

* cited by examiner 100
130
143
144
Sensor
Controller
Power source
Memory
145
Communication interface
146
Angular velocity sensor
Notification interface
131
147

AIn＝(PRn－PSn)／(PFn－PSn)
Pulse beat
1
2
3
4
n
Angle
PFn
PRn
PSn
Time TPR
Δtn

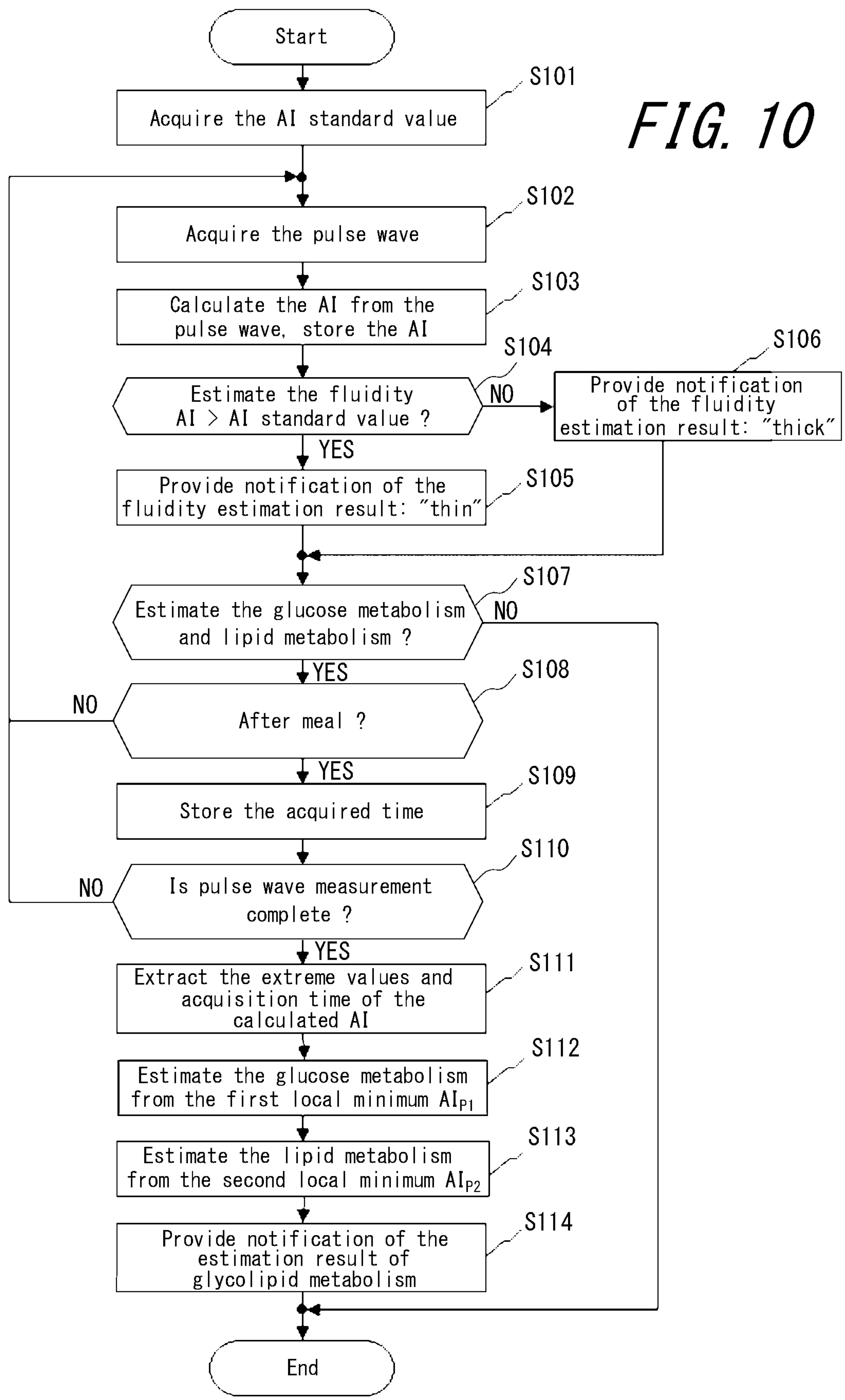

FIG. 10
Start
S101
Acquire the AI standard value
S102
Acquire the pulse wave
S103
Calculate the AI from the pulse wave, store the AI
S104
Estimate the fluidity AI > AI standard value ?
NO
S106
Provide notification of the fluidity estimation result: "thick"
YES
S105
Provide notification of the fluidity estimation result: "thin"
S107
Estimate the glucose metabolism and lipid metabolism ?
NO
YES
S108
NO
After meal ?
YES
S109
Store the acquired time
S110
NO
Is pulse wave measurement complete ?
YES
S111
Extract the extreme values and acquisition time of the calculated AI
S112
Estimate the glucose metabolism from the first local minimum AIP1
S113
Estimate the lipid metabolism from the second local minimum AIP2
S114
Provide notification of the estimation result of glycolipid metabolism
End Start
Measure the postprandial pulse wave
S501
Calculate the postprandial pulse rate
S502
Perform FFT analysis on the postprandial pulse wave
S503
Estimate the preprandial and postprandial blood glucose levels using estimation formulas
S504
End

ELECTRONIC DEVICE AND SYSTEM

CROSS-REFERENCE TO RELATED APPLICATION

This application claims priority to and the benefit of Japanese Patent Application No. 2015-091577 filed Apr. 28, 2015, the entire contents of which are incorporated herein by reference.

TECHNICAL FIELD

This disclosure relates to an electronic device and a system that estimate a subject's state of health from measured biological information.

BACKGROUND

Conventionally, a subject's (user's) state of health is estimated by measuring a blood component or measuring the blood fluidity. These measurements are made using a blood sample collected from the subject. An electronic device that measures biological information from the wrist or other measured part of a subject is also known. For example, the electronic device disclosed in patent literature 1 (PTL 1) measures a subject's pulse rate while attached to the subject's wrist.

CITATION LIST

Patent Literature

PTL 1: JP 2002-360530 A

SUMMARY

Technical Problem

The pain involved in collecting a blood sample, however, prevents subjects from routinely estimating their own state of health. Furthermore, the electronic device disclosed in PTL 1 only measures pulse and is unable to measure the subject's state of health apart from the pulse.

In light of these considerations, it would be helpful to provide an electronic device and a system that can easily estimate a subject's state of health.

Solution to Problem

An electronic device according to an embodiment of this disclosure to solve the above problem may include:

a sensor configured to acquire a pulse wave; and a controller configured to calculate an index based on the acquired pulse wave, such that the controller estimates a state of glucose metabolism or lipid metabolism of a subject using the calculated index.

An electronic device according to an embodiment of this disclosure may include:

a sensor configured to acquire a pulse wave; and a controller configured to calculate an index based on the acquired pulse wave, such that the controller estimates the blood fluidity of a subject using the calculated index.

A system according to an embodiment of this disclosure to solve this problem may include:

a terminal comprising a sensor configured to acquire a pulse wave;

a device configured to estimate a state of glucose metabolism or lipid metabolism of a subject using the acquired pulse wave; and a notification apparatus configured to notify the subject of the estimated state of glucose metabolism or lipid metabolism.

Advantageous Effect

According to this disclosure, an electronic device and a system that can easily measure a subject's state of health in a non-invasive manner can be provided.

BRIEF DESCRIPTION OF THE DRAWINGS

In the accompanying drawings:

FIG. 10 is a flowchart illustrating the procedure to estimate the blood fluidity and the state of glucose metabolism or lipid metabolism in accordance with the AI;

DETAILED DESCRIPTION

Embodiments of this disclosure are described below in detail with reference to the drawings.

Embodiment 1

Figure 1:
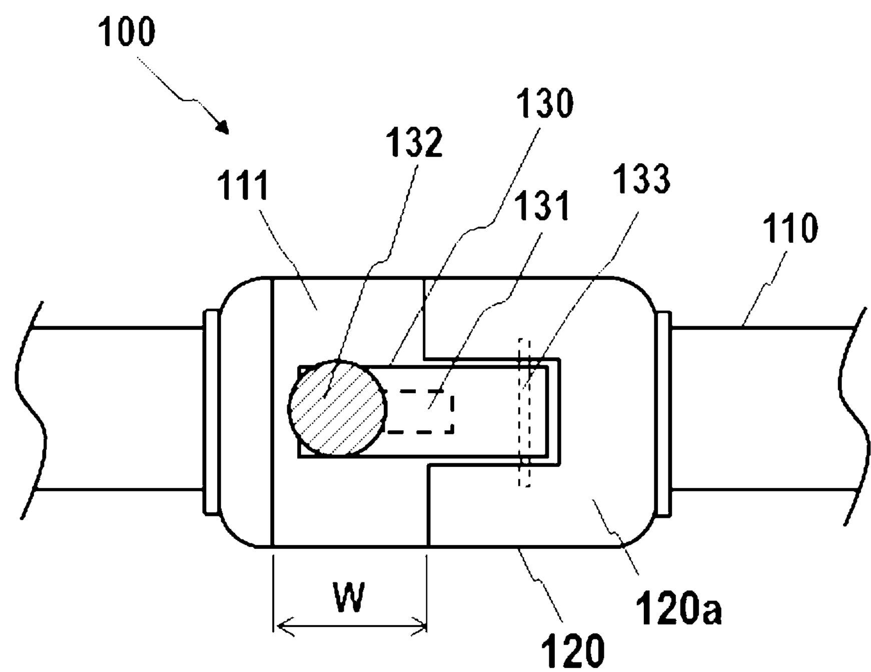
FIG. 1 illustrates the configuration of an electronic device according to Embodiment 1 of this disclosure.

FIG. 1 is a schematic diagram illustrating the configuration of an electronic device according to Embodiment 1 of this disclosure. The electronic device 100 includes a wearing portion 110 and a measurement unit 120. FIG. 1 is a view of the electronic device 100 from a back face 120*a* that comes into contact with a subject.

The electronic device 100 measures the subject's biological information while the electronic device 100 is worn by the subject. The biological information measured by the electronic device 100 is the subject's pulse wave, which is measurable by the measurement unit 120. In this embodiment, as one example, the electronic device 100 is described below as being worn on the subject's wrist and acquiring a pulse wave.

In this embodiment, the wearing portion 110 is a straight, elongated band. Measurement of the pulse wave is performed, for example, in a state in which the subject has wrapped the wearing portion 110 of the electronic device 100 around the wrist. In greater detail, the subject wraps the wearing portion 110 around the wrist so that the back face 120*a* of the measurement unit 120 is in contact with the measured part and then measures the pulse wave. The electronic device 100 measures the pulse wave of blood flowing through the ulnar artery or the radial artery at the subject's wrist.

Figure 2:
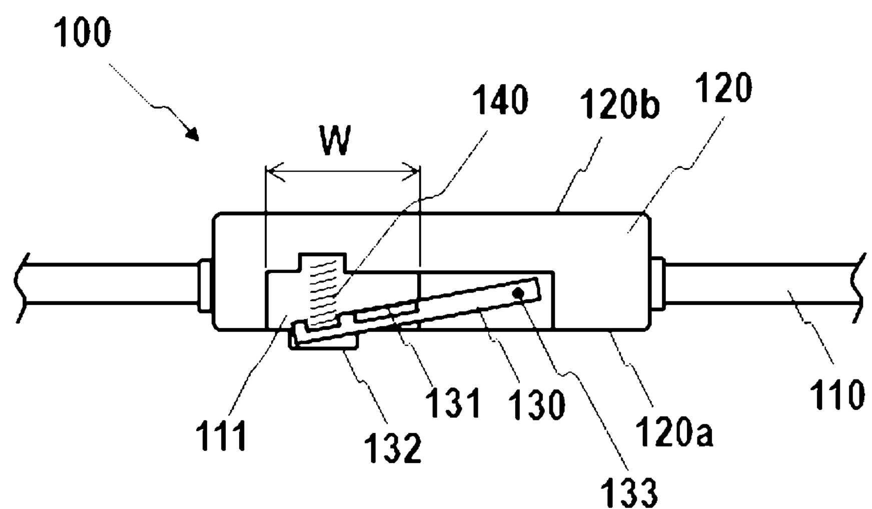
FIG. 2 is a cross-sectional diagram illustrating the configuration of the body in FIG. 1.

FIG. 2 is a cross-sectional diagram schematically illustrating the configuration of the measurement unit 120 in FIG. 1. Along with the measurement unit 120, FIG. 2 also illustrates the wearing portion 110 around the measurement unit 120.

The measurement unit 120 includes the back face 120*a* which contacts the subject's wrist when worn and a front face 120*b* on an opposite side from the back face 120*a*. The measurement unit 120 includes an opening 111 in the back face 120*a* side. In a state in which an elastic body 140 is not compressed, the sensor 130 is supported by the measurement unit 120 with one end of the sensor 130 protruding from the opening 111 at the back face 120*a*. A pulse pad 132 is provided at the one end of the sensor 130. The one end of the sensor 130 is displaceable in a direction nearly perpendicular to the plane of the back face 120*a*. For the one end of the sensor 130 to be displaceable, the other end of the sensor 130 is supported by the measurement unit 120 via a support 133.

The one end of the sensor 130 is in contact with the measurement unit 120 through the elastic body 140 and is displaceable. The elastic body 140 is, for example, a spring. The elastic body 140 is not limited to being a spring, however, and can be any other elastic body, such as resin or a sponge.

While not illustrated, a controller, memory, communication interface, power source, notification interface, circuit for causing these components to operate, cable for connecting these components, and the like may be disposed in the measurement unit 120.

The sensor 130 includes an angular velocity sensor 131 that detects displacement of the sensor 130. It suffices for the angular velocity sensor 131 to be capable of detecting the angular displacement of the sensor 130. The type of sensor provided in the sensor 130 is not limited to the angular velocity sensor 131 and may, for example, be an acceleration sensor, an angle sensor, another motion sensor, or a plurality of these sensors.

Figure 3:
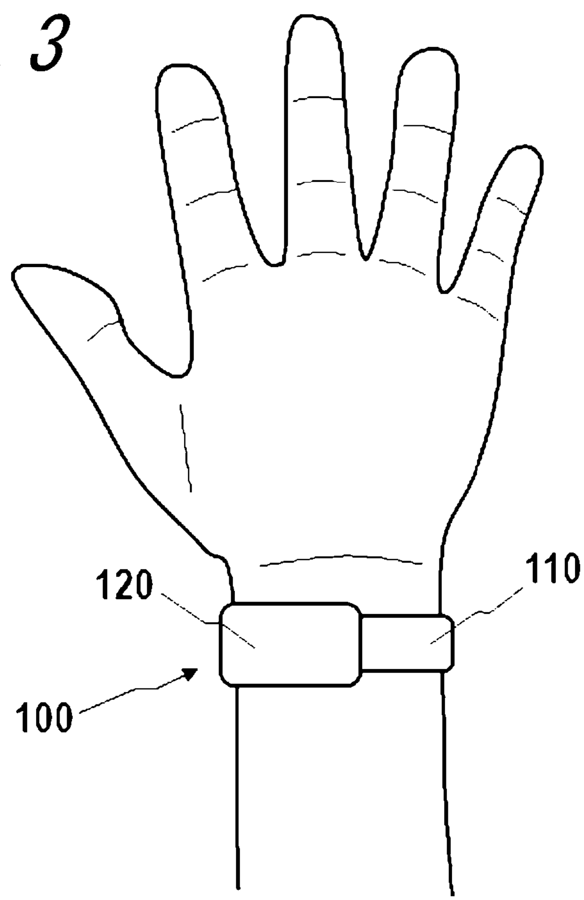
FIG. 3 illustrates an example of a usage state of the electronic device in FIG. 1.

FIG. 3 illustrates an example of a state in which the electronic device 100 is being used by the subject. The subject attaches the electronic device 100 to the wrist for use. The electronic device 100 is worn in a state such that the back face 120*a* of the measurement unit 120 is in contact with the measured part. With the wearing portion 110 wrapped around the wrist, the position of the measurement unit 120 can be adjusted so that the pulse pad 132 is in contact with the position of the ulnar artery or the radial artery.

In FIG. 3, while the electronic device 100 is worn, the one end of the sensor 130 is in contact with the skin above the radial artery. The radial artery is the artery on the thumb side of the subject's left hand. The one end of the sensor 130 is in contact with the skin above the subject's radial artery as a result of the elastic force applied by the elastic body 140 which is arranged between the measurement unit 120 and the sensor 130. The sensor 130 is displaced in accordance with the movement of the subject's radial artery, i.e. pulsation. The angular velocity sensor 131 acquires the pulse wave by detecting displacement of the sensor 130. The pulse wave refers to a waveform representation of the temporal change in volume of a blood vessel due to inflow of blood, acquired from the body surface.

Referring again to FIG. 2, in a state in which the elastic body 140 is not being compressed, the one end of the sensor 130 protrudes from the opening 111. When the electronic device 100 is worn on the subject, the one end of the sensor 130 is in contact with the skin above the subject's radial artery, and in accordance with pulsation, the elastic body 140 expands and contracts, and the one end of the sensor 130 is displaced. A component with an appropriate elastic modulus is used for the elastic body 140 so as to allow it to expand and contract in accordance with pulsation without inhibiting pulsation. The opening width W of the opening 111 is sufficiently greater than the vessel diameter, i.e. the radial artery diameter in this embodiment. By providing the opening 111 in the measurement unit 120, the back face 120*a* of the measurement unit 120 does not compress the radial artery when the electronic device 100 is worn. Therefore, the electronic device 100 can acquire a pulse wave with little noise, thus improving measurement accuracy.

FIG. 3 illustrates an example in which the electronic device 100 is worn on the wrist and acquires a pulse wave at the radial artery, but this disclosure is not limited to this example. For example, the electronic device 100 may acquire the pulse wave of blood flowing through a carotid artery in the subject's neck. In greater detail, the subject may press the pulse pad 132 lightly against the position of the carotid artery to measure the pulse wave. The subject may also wrap the wearing portion 110 around the neck so that the pulse pad 132 is at the position of the carotid artery.

Figure 4:
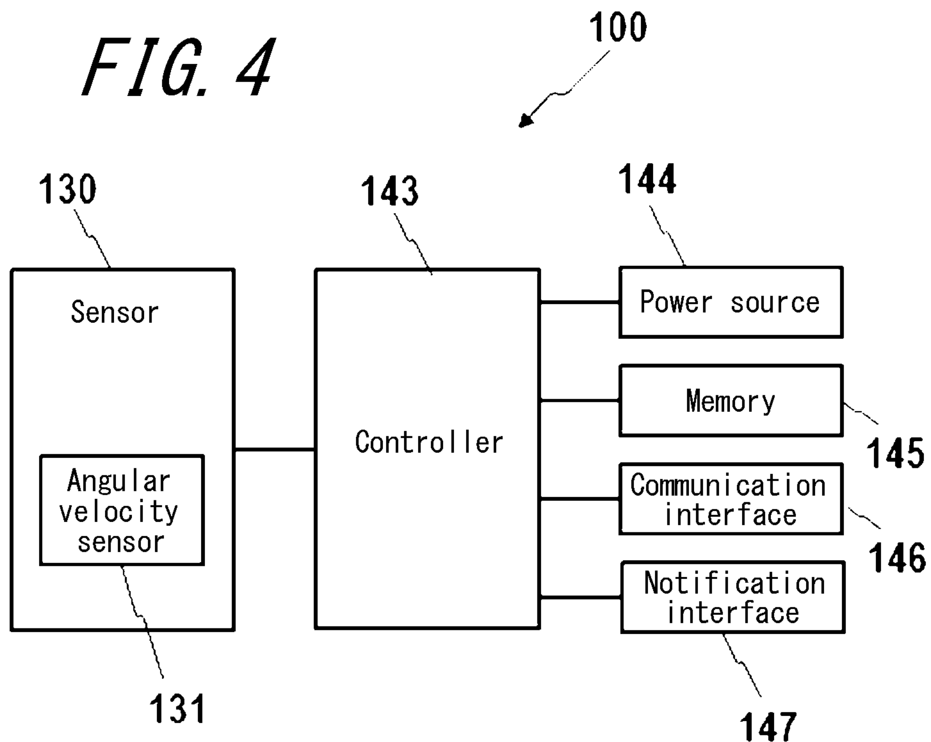
FIG. 4 is a functional block diagram illustrating the configuration of the electronic device in FIG. 1.

FIG. 4 is a functional block diagram illustrating the configuration of the electronic device 100. The electronic device 100 includes the sensor 130, a controller 143, a power source 144, a memory 145, a communication interface 146, and a notification interface 147. In this embodiment, the controller 143, power source 144, memory 145, communication interface 146, and notification interface 147 are included inside the measurement unit 120 or the wearing portion 110.

The sensor 130 includes the angular velocity sensor 131, detects pulsation from the measured part, and acquires the pulse wave.

The controller 143 is a processor for overall control and management of the electronic device 100, including, for example, the functional blocks of the electronic device 100. Furthermore, the controller 143 is a processor that calculates an index based on a pulse wave propagation phenomenon using the acquired pulse wave. The controller 143 is configured using a processor such as a central processing unit (CPU) that executes a program prescribing control procedures and a program that calculates the index based on the pulse wave propagation phenomenon. These programs are, for example, stored in a storage medium such as the memory 145. In accordance with the calculated index, the controller 143 estimates a state related to the subject's glucose metabolism, lipid metabolism, or the like. The controller 143 also notifies the notification interface 147 of data.

The power source 144 for example includes a lithium-ion battery and a control circuit for charging and discharging the lithium-ion battery. The power source 144 supplies power to the electronic device 100 overall.

The memory 145 stores programs and data. The memory 145 may include any non-transitory storage medium, such as a semiconductor storage medium and a magnetic storage medium. The memory 145 may also include a plurality of types of storage media. The memory 145 may include a combination of a portable storage medium, such as a memory card, optical disc, or magneto-optical disc, and an apparatus for reading the storage medium. The memory 145 may include a storage device used as a volatile storage area, such as random access memory (RAM). The memory 145 stores a variety of information, programs for causing the electronic device 100 to operate, and the like and also functions as a working memory. The memory 145 may, for example, store the measurement result of the pulse wave acquired by the sensor 130.

The communication interface 146 exchanges a variety of data with an external apparatus by wired or wireless communication. For example, the communication interface 146 communicates with an external apparatus that stores the biological information of the subject to manage the state of health. The communication interface 146 transmits the measurement result of the pulse wave measured by the electronic device 100 and the state of health estimated by the electronic device 100 to the external apparatus.

The notification interface 147 provides notification of information by sound, vibration, images, and the like. The notification interface 147 may include a speaker, a vibrator, and/or a display device such as a liquid crystal display (LCD), an organic electro-luminescence display (OELD), or an inorganic electro-luminescence display (IELD). In this embodiment, for example, the notification interface 147 provides notification of the state of the subject's glucose metabolism or lipid metabolism.

Figure 5:
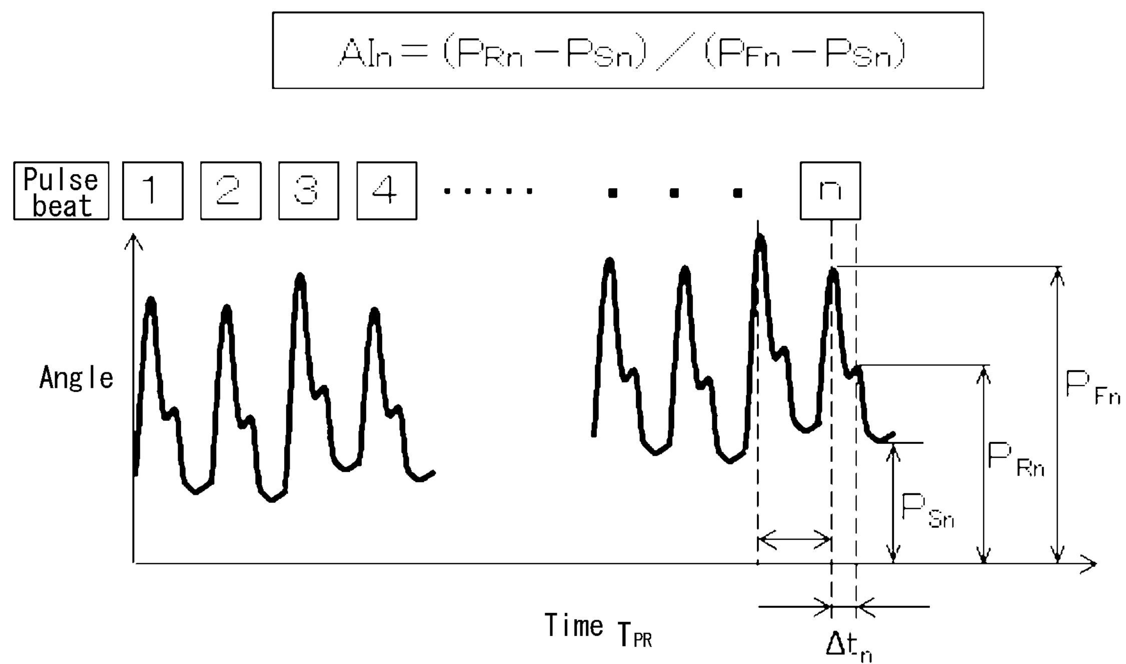
FIG. 5 illustrates an example of pulse waves acquired by a sensor.

FIG. 5 illustrates an example of pulse waves acquired at the wrist using the electronic device 100. FIG. 5 illustrates the case where the angular velocity sensor 131 is used as the means for detecting the pulsation. FIG. 5 is a time integration of the angular velocity acquired by the angular velocity sensor 131, with the horizontal axis representing time and the vertical axis representing the angle. Since the acquired pulse wave may, for example, include noise that is due to body movement of the subject, the pulse wave may be corrected by a filter that removes the direct current (DC) component, so as to extract only the pulsation component.

A method for calculating a pulse wave index by using the acquired pulse wave is described with reference to FIG. 5. Propagation of the pulse wave is a phenomenon in which pulsation due to blood being pumped from the heart is transmitted through artery walls or blood. The pulsation due to blood pumped from the heart reaches the peripheries of limbs as a forward wave, a portion of which is reflected at locations such as where a blood vessel branches, or where the diameter of a blood vessel changes, and returns as a reflected wave. The pulse wave index is, for example, the pulse wave velocity (PWV) of the forward wave, the magnitude PR of the reflected wave of the pulse wave, the time difference Δt between the forward wave and the reflected wave of the pulse wave, or the augmentation index (AI) represented as the ratio between the magnitudes of the forward wave and the reflected wave of the pulse wave.

The pulse wave illustrated in FIG. 5 represents n pulse beats of the user, where n is an integer and is equal to or greater than one. The pulse wave is a combined wave, in which the forward wave generated by ejection of blood from the heart overlaps with the reflected wave generated at blood vessel branches and locations of change in blood vessel diameter. In FIG. 5, the magnitude of the peak in the pulse wave from the forward wave in each pulse beat is labeled $P_{Fn}$, the magnitude of the peak in the pulse wave from the reflected wave in each pulse beat is labeled $P_{Rn}$, and the smallest value of the pulse wave in each pulse beat is labeled $P_{Sn}$. In FIG. 5, the interval between peaks of the pulse wave is labeled $T_{PR}$.

The pulse wave index quantifies information obtained from the pulse wave. An example of a pulse wave index is PWV, which is calculated in accordance with the difference in propagation time of pulse waves measured at two points, such as the upper arm and ankle, and the distance between the two points. In greater detail, PWV is calculated by synchronously acquiring the pulse wave at two points on an artery (e.g. the upper arm and ankle) and dividing the distance between the two points (L) by the time difference of the pulse waves at the two points (PTT). A further example of a pulse wave index is the reflected wave magnitude $P_R$, which may be calculated as the magnitude $P_{Rn}$ of the peak in the pulse wave from the reflected wave or as the average of n values, $P_{Rave}$. A further example of a pulse wave index is the time difference Δt between the forward wave and the reflected wave of the pulse wave, which may be calculated as the time difference Δtn between predetermined pulse beats or as the average of n time differences, $\Delta t_{ave}$. A further example of a pulse wave index is the AI, which is the result of dividing the magnitude of the reflected wave by the magnitude of the forward wave and is represented as $AI_n=(P_{Rn}-P_{Sn})/(P_{Fn}-P_{Sn})$. $AI_n$ is the AI for each pulse beat. As a pulse wave index, AI may, for example, be calculated by measuring the pulse wave for several seconds and calculating the average $AI_{ave}$ of the $AI_n$ for each pulse beat (n=an integer from 1 to n).

The PWV, the reflected wave magnitude $P_R$, the time difference Δt between the forward wave and the reflected wave, and the AI indices can be used to estimate the state of arteriosclerosis because they change in dependence on the hardness of the blood vessel walls. The PWV increases, for example, if the blood vessel walls are hard. The reflected wave magnitude $P_R$, for example, also increases if the blood vessel walls are hard. The time difference Δt between the forward wave and the reflected wave, for example, decreases if the blood vessel walls are hard. The AI, for example, increases if the blood vessel walls are hard. Furthermore, by using these indices which are based on the pulse wave, the electronic device 100 can estimate the state of arteriosclerosis and also estimate the fluidity (viscosity) of blood. In particular, the electronic device 100 can estimate the change in blood fluidity from the change in indices based on pulse waves acquired for the same measured part of the same subject during a time period (such as several days) over which the state of arteriosclerosis exhibits essentially no change. Here, blood fluidity indicates the ease of blood flow. The PWV, for example, decreases if the blood fluidity is low. The reflected wave magnitude $P_R$, for example, also decreases if the blood fluidity is low. The time difference Δt between the forward wave and the reflected wave, for example, increases if the blood fluidity is low. The AI, for example, decreases if the blood fluidity is low.

In this embodiment, as an example of pulse wave indices, the electronic device 100 calculates the PWV, the reflected wave magnitude $P_R$, the time difference Δt between the forward wave and the reflected wave, and the AI. However, the pulse wave indices are not limited to these examples. For example, the electronic device 100 may use posterior systolic blood pressure as a pulse wave index.

Figure 6:
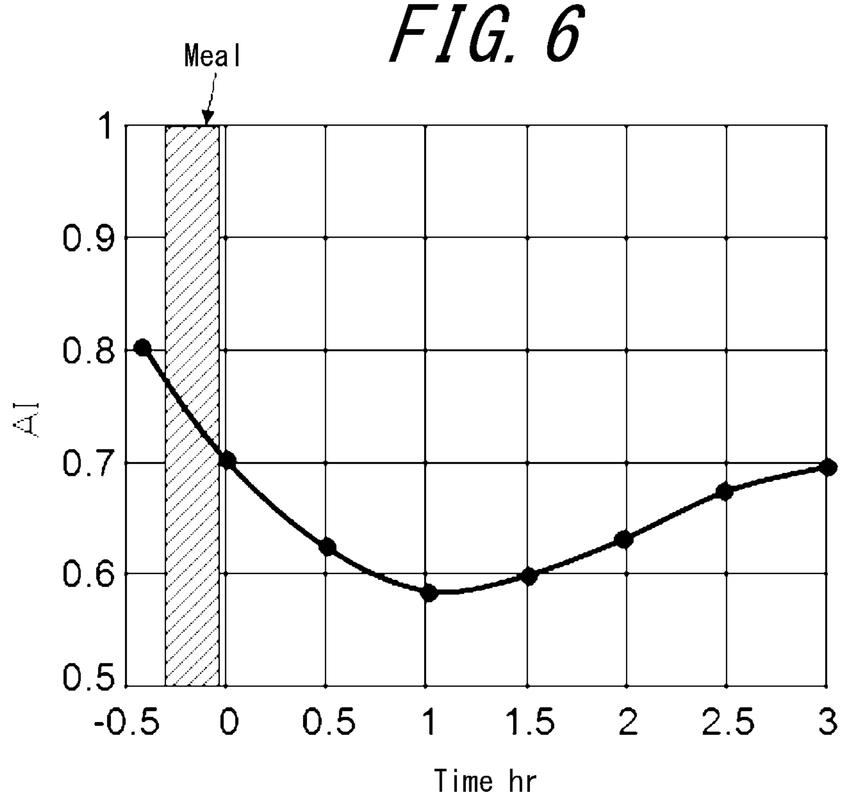
FIG. 6 illustrates the change over time in the calculated augmentation index (AI)

FIG. 6 illustrates the change over time in the calculated AI. In this embodiment, the pulse wave is acquired for approximately five seconds using the electronic device 100 provided with the angular velocity sensor 131. The controller 143 calculates the AI from the acquired pulse wave for each pulse beat and further calculates the average $AI_{ave}$ thereof. In this embodiment, the electronic device 100 acquires the pulse wave at a plurality of times before a meal and after the meal and calculates the average AI (simply "AI" below) as an example of an index based on the acquired pulse wave. The horizontal axis in FIG. 6 represents elapsed time, with the initial measured time after a meal as 0. The vertical axis in FIG. 6 indicates the AI calculated from the pulse waves acquired at that time. The pulse waves were acquired on the radial artery, with the subject at rest.

The electronic device 100 acquired the pulse waves before a meal, immediately after the meal, and every 30 minutes after the meal, and calculated a plurality of AI values on the basis of the pulse waves. The AI calculated from the pulse wave acquired before the meal was approximately 0.8. The AI immediately after the meal was lower than before the meal, and the AI reached its lowest value approximately one hour after the meal. The AI gradually increased in the three hours after the meal, until completion of the measurement.

The electronic device 100 can estimate the change in blood fluidity from the change in the calculated AI. The blood fluidity reduces, for example, when red blood cells, white blood cells, and platelets in the blood harden into balls, or when the adhesive force increases. The blood fluidity also reduces, for example, when the moisture content of platelets in the blood decreases. These changes in the blood fluidity depend on the subject's state of health, such as the below-described glycolipid state, heatstroke, dehydration, hypothermia, and the like. Before the subject's state of health becomes critical, the subject can use the electronic device 100 of this embodiment to learn about the subject's own changes in blood fluidity. From the changes in AI before and after a meal as illustrated in FIG. 6, it can be inferred that the blood fluidity decreases after a meal, reaching a minimum approximately one hour after a meal and gradually increasing thereafter. The electronic device 100 may notify the user by expressing a low state of blood fluidity as "thick" and a high state of blood fluidity as "thin". For example, the electronic device 100 may make the determination of "thick" or "thin" taking the average AI for the subject's actual age as a standard. The electronic device 100 may determine the blood to be "thin" when the calculated AI is greater than the average and "thick" when the calculated AI is less than the average. The electronic device 100 may, for example, make the determination of "thick" or "thin" taking the preprandial AI as a standard. The electronic device 100 may compare the postprandial AI with the preprandial AI to estimate the degree of "thickness". The electronic device 100 can, for example, use the preprandial AI, i.e. the AI when fasting, as an index of the subject's vascular age (blood vessel hardness). For example, by calculating the amount of change in the AI calculated using the subject's preprandial AI, i.e. the AI when fasting, as a standard, the electronic device 100 can reduce the estimation error due to the subject's vascular age (blood vessel hardness). Hence, the change in blood fluidity can be estimated more accurately.

Figure 7:
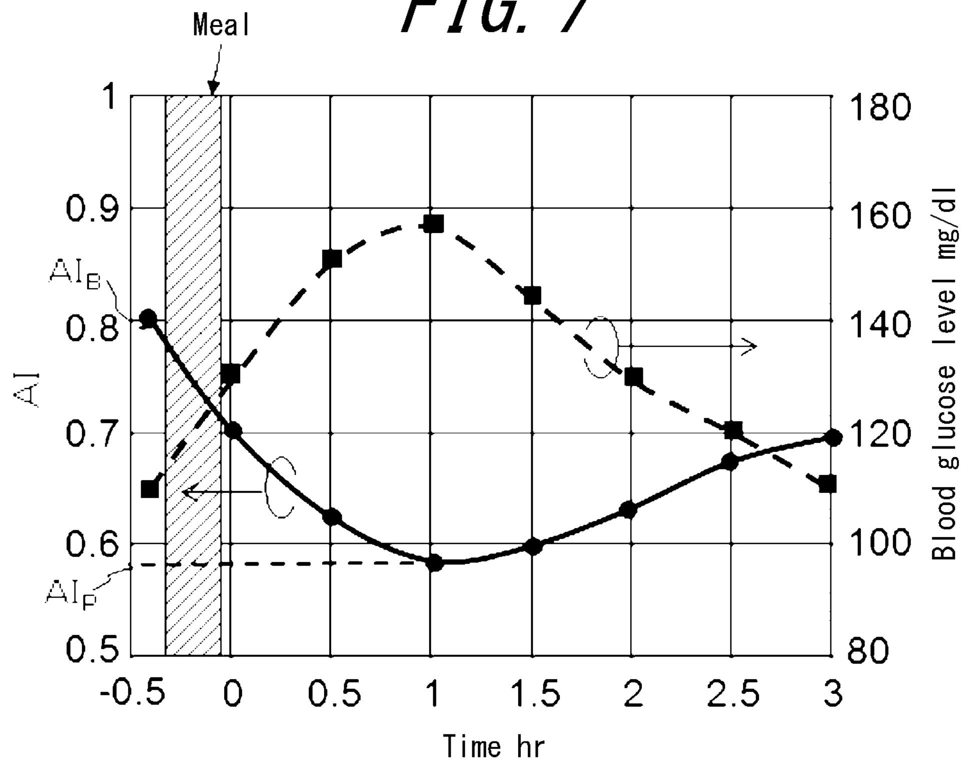
FIG. 7 illustrates the calculated AI and the result of measuring the blood glucose level.

FIG. 7 illustrates the calculated AI and the result of measuring the blood glucose level. The method for acquiring the pulse waves and the method for calculating AI are the same as in the embodiment illustrated in FIG. 6. The right vertical axis in FIG. 7 represents the blood glucose level, and the left vertical axis represents the calculated AI. The solid curve in FIG. 7 indicates the AI calculated from the acquired pulse waves, and the dotted curve indicates the measured blood glucose level. The blood glucose level was measured immediately after the pulse wave was acquired. The blood glucose level was measured using the blood glucose meter Medisafe Fit manufactured by Terumo Corporation. As compared to the preprandial blood glucose level, the postprandial blood glucose level rose by approximately 20 mg/dl. The blood glucose level reached the largest value approximately one hour after the meal. Subsequently, until measurement was completed, the blood glucose level reduced slowly and became nearly the same as the preprandial blood glucose level at approximately three hours after the meal.

As illustrated in FIG. 7, the preprandial and postprandial blood glucose levels are negatively correlated with the AI calculated from the pulse wave. As the blood glucose level rises, the red blood cells and white blood cells harden into balls because of sugar in the blood, or the adhesive force increases. As a result, the blood fluidity reduces. Upon a reduction in the blood fluidity, the PWV may decrease. Upon a decrease in the PWV, the time difference Δt between the forward wave and the reflected wave may increase. Upon an increase in the time difference Δt between the forward wave and the reflected wave, the reflected wave magnitude $P_R$ may decrease relative to the forward wave magnitude $P_F$. Upon a decrease in the reflected wave magnitude $P_R$ relative to the forward wave magnitude $P_F$, the AI may decrease. Since the AI within the several hours following the meal (three hours in this embodiment) is correlated with the blood glucose level, variation in the subject's blood glucose level can be inferred from a change in AI. Furthermore, by measuring the subject's blood glucose level and acquiring the correlation with the AI in advance, the electronic device 100 can estimate the subject's blood glucose level from the calculated AI.

The electronic device 100 can estimate the state of the subject's glucose metabolism in accordance with the occurrence time of $AI_P$, which is the first detected local minimum of the AI after a meal. For example, the electronic device 100 estimates the blood glucose level as the state of glucose metabolism. As an example of estimating the state of glucose metabolism, the electronic device 100 can infer that the subject has abnormal glucose metabolism (patient with diabetes) when the first detected local minimum $AI_P$ of the AI after a meal is detected after a predetermined length of time or longer (for example, approximately 1.5 hours or longer after a meal).

The electronic device 100 can estimate the state of the subject's glucose metabolism in accordance with the difference $AI_B-AI_P$ between $AI_B$, which is the preprandial AI, and $AI_P$, which is the first detected local minimum of the postprandial AI. As an example of estimating the state of glucose metabolism, the electronic device 100 can infer that the subject has abnormal glucose metabolism (patient with postprandial hyperglycemia) when $AI_B-AI_P$ is equal to or greater than a predetermined value (for example, 0.5 or higher).

Figure 8:
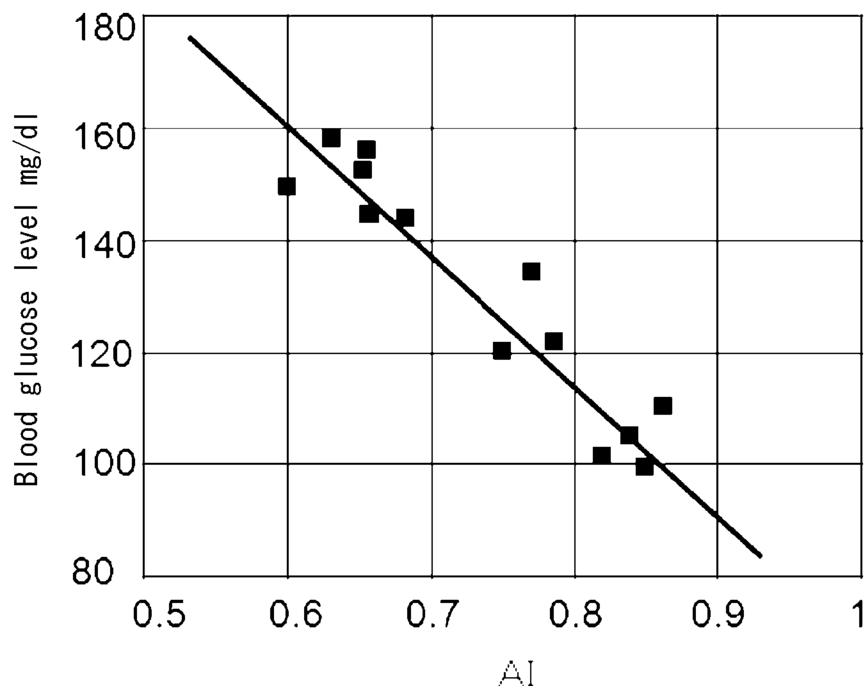
FIG. 8 illustrates the relationship between the calculated AI and the blood glucose level.

FIG. 8 illustrates the relationship between the calculated AI and the blood glucose level. The calculated AI and the blood glucose level were acquired within one hour after a meal, when the blood glucose level varies greatly. The data in FIG. 8 include a plurality of different data points after a meal for the same subject. As illustrated in FIG. 8, the calculated AI and the blood glucose level are negatively correlated. The correlation coefficient between the calculated AI and the blood glucose level is 0.9 or higher, indicating an extremely high correlation. For example, by acquiring the correlation between the calculated AI and blood glucose level illustrated in FIG. 8 for each subject in advance, the electronic device 100 can also estimate the subject's blood glucose level from the calculated AI.

Figure 9:
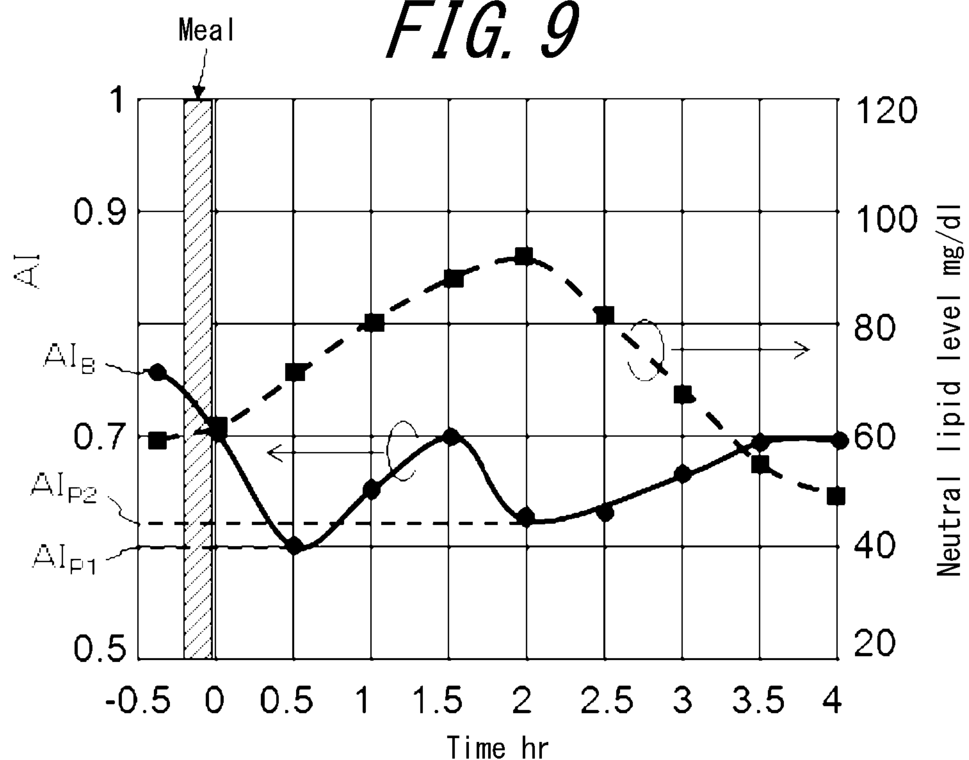
FIG. 9 illustrates the calculated AI and the result of measuring the lipid level.

FIG. 9 illustrates the calculated AI and the result of measuring neutral lipids. The method for acquiring the pulse waves and the method for calculating AI are the same as in the embodiment illustrated in FIG. 6. The right vertical axis in FIG. 9 represents the neutral lipid level in the blood, and the left vertical axis represents the AI. The solid curve in FIG. 9 indicates the AI calculated from the acquired pulse waves, and the dotted curve indicates the measured neutral lipid level. The neutral lipid level was measured immediately after the pulse wave was acquired. The neutral lipid level was measured using the "Pocket Lipid" lipid measurement apparatus, manufactured by Techno Medica Co., Ltd. As compared to the preprandial neutral lipid level, the highest value of the postprandial neutral lipid level represented a rise of approximately 30 mg/dl. The neutral lipid level reached the highest value approximately two hours after the meal. Subsequently, until measurement was completed, the neutral lipid level decreased slowly and became nearly the same as the preprandial neutral lipid level at approximately three and a half hours after the meal.

By contrast, the local minimums of the calculated AI were a first local minimum $AI_{P1}$ detected approximately 30 minutes after the meal and a second local minimum $AI_{P2}$ detected approximately two hours after the meal. It can be inferred that the first local minimum $AI_{P1}$ detected approximately 30 minutes after the meal is caused by the above-described blood glucose level after the meal. The occurrence time of the second local minimum $AI_{P2}$, which was detected approximately two hours after the meal, is nearly coincident with that of the highest neutral lipid level detected approximately two hours after the meal. From this, it can be inferred that the second local minimum $AI_{P2}$ detected a predetermined length of time or longer after a meal is due to the effect of neutral lipids. Like the blood glucose level, it can be understood that the preprandial and postprandial neutral lipid values are negatively correlated with the AI calculated from the pulse wave. In particular, the local minimum $AI_{P2}$ of the AI calculated a predetermined length of time or longer (in this embodiment, approximately 1.5 hours or longer) after a meal is correlated with neutral lipids. Therefore, the variation in the subject's neutral lipid level can be estimated from the variation in AI. Furthermore, by measuring the subject's neutral lipid level in advance and determining a correlation with the AI, the electronic device 100 can estimate the subject's neutral lipid level from the calculated AI.

The electronic device 100 can estimate the subject's state of lipid metabolism on the basis of the occurrence time of the second local minimum $AI_{P2}$ detected a predetermined length of time or longer after a meal. For example, the electronic device 100 estimates the lipid level as the state of lipid metabolism. As an example, the electronic device 100 can infer that the subject has abnormal lipid metabolism (patient with hyperlipidemia) when the second local minimum $AI_{P2}$ is detected a predetermined length of time or longer (for example, four hours or longer) after a meal.

The electronic device 100 can estimate the subject's state of lipid metabolism in accordance with the difference $AI_B-AI_{P2}$ between the $AI_B$, which is the preprandial AI, and the second local minimum $AI_{P2}$ detected a predetermined length of time or longer after the meal. As an example, the electronic device 100 can infer that the subject's state of lipid metabolism is abnormal (patient with postprandial hyperlipidemia) when $AI_B-AI_{P2}$ is 0.5 or greater.

From the measurement results illustrated in FIG. 7 through FIG. 9, the electronic device 100 of this embodiment can estimate the subject's state of glucose metabolism in accordance with the first local minimum $AI_{P1}$, detected earliest after a meal, and the occurrence time thereof. Furthermore, the electronic device 100 of this embodiment can estimate the subject's state of lipid metabolism in accordance with the second local minimum $AI_{P2}$, detected a predetermined length of time or longer after the first local minimum $AI_{P1}$, and the occurrence time thereof.

The case of neutral lipids has been described as an example of estimating the lipid metabolism in this embodiment, but estimation of the lipid metabolism is not limited to neutral lipids. The lipid level estimated by the electronic device 100 includes, for example, total cholesterol, high-density lipoprotein (HDL) cholesterol, and low-density lipoprotein (LDL) cholesterol. These lipid values also exhibit tendencies similar to the above-described case of neutral lipids.

FIG. 10 is a flowchart illustrating the procedure for estimating the blood fluidity and the state of glucose metabolism and lipid metabolism on the basis of the AI. With reference to FIG. 10, the process by which the electronic device 100 according to this embodiment estimates the blood fluidity and the state of glucose metabolism and lipid metabolism is described.

As illustrated in FIG. 10, the electronic device 100 acquires the subject's AI standard value as an initial setting (step S101). An average AI estimated from the subject's age or the subject's AI when fasting, acquired in advance, may be used as the AI standard value. The electronic device 100 may also use the AI determined to be before a meal in steps S102 to S108 or the AI calculated immediately before pulse wave measurement as the AI standard value. In this case, the electronic device 100 executes step S101 after steps S102 to S108.

Subsequently, the electronic device 100 acquires the pulse wave (step S102). For example, the electronic device 100 determines whether a pulse wave of predetermined amplitude or higher has been obtained during a predetermined measurement time (for example, five seconds). If a pulse wave of predetermined amplitude or higher has been obtained, the process proceeds to step S103. If a pulse wave of predetermined amplitude or higher has not been obtained, step S102 is repeated (these steps are not illustrated).

From the pulse wave acquired in step S102, the electronic device 100 calculates the AI as a pulse wave index and stores the AI in the memory 145 (step S103). The electronic device 100 may calculate the average $AI_{ave}$ from the $AI_n$ (n=an integer from 1 to n) for each of a predetermined number of pulse beats (for example, three beats) and use the average $AI_{ave}$ as the AI. Alternatively, the electronic device 100 may calculate the AI for a specific pulse beat.

The AI may be calculated by correcting the AI in accordance, for example, with the pulse rate $P_R$, the pulse pressure ($P_F-P_S$), body temperature, the temperature of the measured part, and the like. Pulse and AI are known to be negatively correlated, as are pulse pressure and AI. Temperature and AI are known to be positively correlated. When correcting the AI, for example the electronic device 100 calculates the pulse and the pulse pressure in addition to the AI in step S103. For example, the electronic device 100 may include a temperature sensor in the sensor 130 and may acquire the temperature of the measured part when acquiring the pulse wave in step S102. The AI is corrected by substituting the acquired pulse, pulse pressure, temperature, and the like into a correction formula derived in advance.

Subsequently, the electronic device 100 compares the AI standard value acquired in step S101 with the AI calculated in step S103 and estimates the fluidity of the subject's blood (step S104). When the calculated AI is greater than the AI standard value (YES), then the electronic device 100 infers that the blood fluidity is high and for example provides a notification that "the blood is thin" (step S105). When the calculated AI is not greater than the AI standard value (NO), then the electronic device 100 infers that the blood fluidity is low and for example provides a notification that "the blood is thick" (step S106).

Subsequently, the electronic device 100 confirms with the subject whether to estimate the state of glucose metabolism and lipid metabolism (step S107). When it is confirmed in step S107 that the state of glucose metabolism and lipid metabolism is not to be estimated (NO), the electronic device 100 terminates the process. When it is confirmed in step 207 that the state of glucose metabolism and lipid metabolism is to be estimated (YES), the electronic device 100 confirms whether the calculated AI was acquired before a meal or after a meal (step S108). When acquisition was not after a meal, i.e. was before a meal (NO), the process returns to step S102, and the next pulse wave is acquired. When acquisition was after a meal (YES), the electronic device 100 stores the acquisition time of the pulse wave corresponding to the calculated AI (step S109). When continuing to acquire pulse waves (NO in step S110), the process returns to step S102, and the next pulse wave is acquired. When terminating pulse wave measurement (YES in step S110), the process proceeds to step S111 and beyond, and the electronic device 100 estimates the subject's state of glucose metabolism and lipid metabolism.

Subsequently, the electronic device 100 extracts the local minimums and the times thereof from a plurality of AI values calculated in step S104 (step S111). For example, in the case of the AI values illustrated by the solid curve in FIG. 9 being calculated, the electronic device 100 extracts the first local minimum $AI_{P1}$ occurring 30 minutes after the meal and the second local minimum $AI_{P2}$ occurring approximately two hours after the meal.

Subsequently, the electronic device 100 estimates the subject's state of glucose metabolism from the first local minimum $AI_N$ and the time thereof (step S112). Furthermore, the electronic device 100 estimates the subject's state of lipid metabolism from the second local minimum $AI_{P2}$ and the time thereof (step S113). Examples of estimating the subject's state of glucose metabolism and lipid metabolism follow the examples described above in relation to FIG. 9 and are therefore is omitted.

Subsequently, the electronic device 100 provides notification of the estimation result from step S112 and step S113 (step S114) and terminates the process illustrated in FIG. 10. For example, the notification interface 147 provides notifications such as "normal glucose metabolism", "suspected abnormal glucose metabolism", "normal lipid metabolism", or "suspected abnormal lipid metabolism". The notification interface 147 can also provide advice such as "seek advice from a doctor" or "improve your diet". The electronic device 100 then terminates the process illustrated in FIG. 10.

In the above embodiment, the electronic device 100 can estimate the fluidity of the subject's blood and the state of glucose metabolism and lipid metabolism from an index based on the subject's pulse wave. Therefore, the electronic device 100 can estimate the fluidity of the subject's blood and the state of glucose metabolism and lipid metabolism in a non-invasive manner and in a short time.

In the above embodiment, the electronic device 100 can estimate the state of glucose metabolism and estimate the state of lipid metabolism from the extreme values of indices based on the subject's pulse waves and the times thereof. Therefore, the electronic device 100 can estimate the subject's state of glucose metabolism and lipid metabolism in a non-invasive manner and in a short time.

In the above embodiment, the electronic device 100 can, for example, estimate the subject's state of glucose metabolism and lipid metabolism using an index based on the subject's pulse wave before a meal (when fasting) as a standard. Therefore, the electronic device 100 can accurately estimate the fluidity of the subject's blood and the state of glucose metabolism and lipid metabolism without regard for the blood vessel diameter and blood vessel hardness, which do not exhibit short-term change.

In the above embodiment, the electronic device 100 can estimate the subject's blood glucose level and lipid level in a non-invasive manner and in a short time by calibrating the index based on the subject's pulse wave with the blood glucose level and lipid level.

Embodiment 2

According to Embodiment 1, an example of an electronic device 100 which estimates a subject's glucose metabolism and lipid metabolism in accordance with the AI calculated from a pulse wave as a pulse wave index is described. In Embodiment 2, an example of an electronic device 100 which estimates a subject's glucose metabolism in accordance with estimation formulas determined using regression analysis is described. In this embodiment, the electronic device 100 estimates the blood glucose level as the subject's glucose metabolism. Since the configuration of the electronic device 100 according to this embodiment is similar to that of Embodiment 1, a description of the configuration is omitted.

The electronic device 100 stores estimation formulas for estimating the blood glucose level based on pulse wave in the memory 145, for example, in advance. The electronic device 100 estimates the blood glucose level using these estimation formulas.

First, estimation theory related to estimating the blood glucose level on the basis of a pulse wave is described. As a result of an increase in the blood glucose level after a meal, the blood fluidity reduces (viscosity increases), blood vessels dilate, and the amount of circulating blood increases. Vascular dynamics and hemodynamics are determined so as to balance these states. The reduction in blood fluidity occurs, for example, because of an increase in the viscosity of blood plasma or a reduction in the deformability of red blood cells. Dilation of blood vessels occurs for reasons such as secretion of insulin, secretion of digestive hormones, and a rise in body temperature. When blood vessels dilate, the pulse rate increases to suppress a reduction in blood pressure. Furthermore, the increase in the amount of circulating blood compensates for blood consumption for digestion and absorption. Changes, in vascular dynamics and hemodynamics from before to after a meal due to these factors is also reflected in the pulse wave. Therefore, the electronic device 100 can acquire the pulse wave and estimate the blood glucose level based on the change in the acquired pulse wave.

Estimation formulas for estimating the blood glucose level in accordance with the above estimation theory can be derived by performing regression analysis on sample data representing preprandial/postprandial blood glucose levels and pulse waves obtained from a plurality of subjects. The subject's blood glucose level can be estimated by applying the derived estimation formulas to the subject's pulse wave index at the time of estimation. If the estimation formulas are derived in particular by performing regression analysis using sample data for which variation in the blood glucose level is close to a normal distribution, the blood glucose level of the subject being tested can be estimated either before or after a meal.

Figure 11:
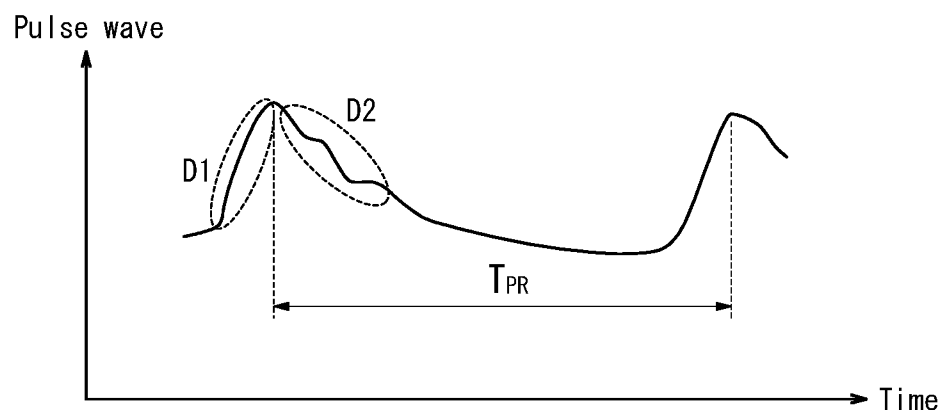
FIG. 11 illustrates an example of an estimation method based on change in the pulse wave in an electronic device according to Embodiment 2 of this disclosure.
Figure 12:
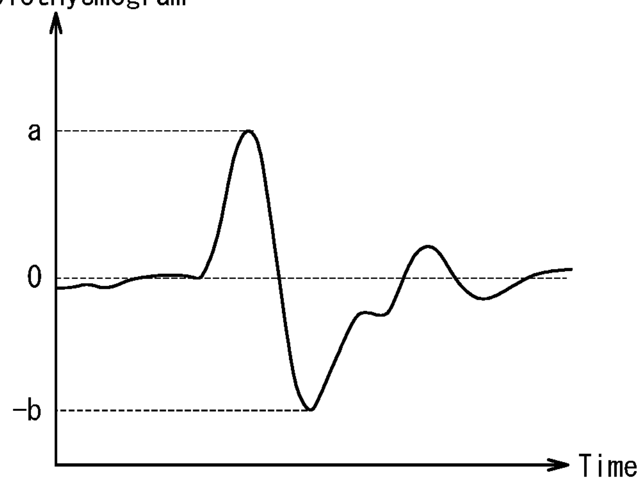
FIG. 12 illustrates an example of the second derivative of photoplethysmogram.

FIG. 11 illustrates an example of a pulse wave and an example of an estimation method based on a change in pulse wave. The estimation formulas for estimating blood glucose level are, for example, determined using regression analysis related to an index SI indicating the rising of a pulse wave (rising index), the AI, and the pulse rate PR. The rising index SI is derived using the waveform indicated in the area D1 of FIG. 11. In greater detail, the rising index SI is the ratio of the first local minimum to the first local maximum in the second derivative of photoplethysmogram yielded by the second derivative of the pulse wave. For example, for the second derivative of photoplethysmogram illustrated as an example in FIG. 12, the rising index SI is expressed as −b/a. The rising index SI decreases because of a reduction in fluidity of the blood, secretion of insulin, dilation (relaxation) of blood vessels due to increased body temperature, and the like after a meal. The AI is derived from the waveform indicated in area D2 of FIG. 11. The AI reduces because of a reduction in fluidity of the blood, dilation of blood vessels due to increased body temperature, and the like after a meal. The pulse rate PR is derived from the period $T_{PR}$ of FIG. 11. The pulse rate PR rises after a meal. The estimation formulas derived using the rising index SI, the AI, and/or the pulse rate PR allow estimation of the blood glucose level.

Figure 13A:
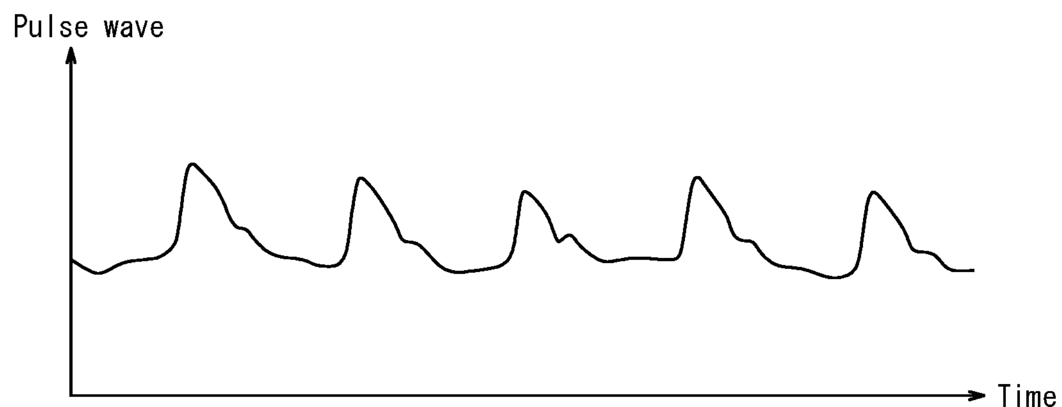
FIG. 13A illustrates a pulse wave for explaining another example of an estimation method based on change in the pulse wave in an electronic device according to Embodiment 2 of this disclosure.
Figure 13B:
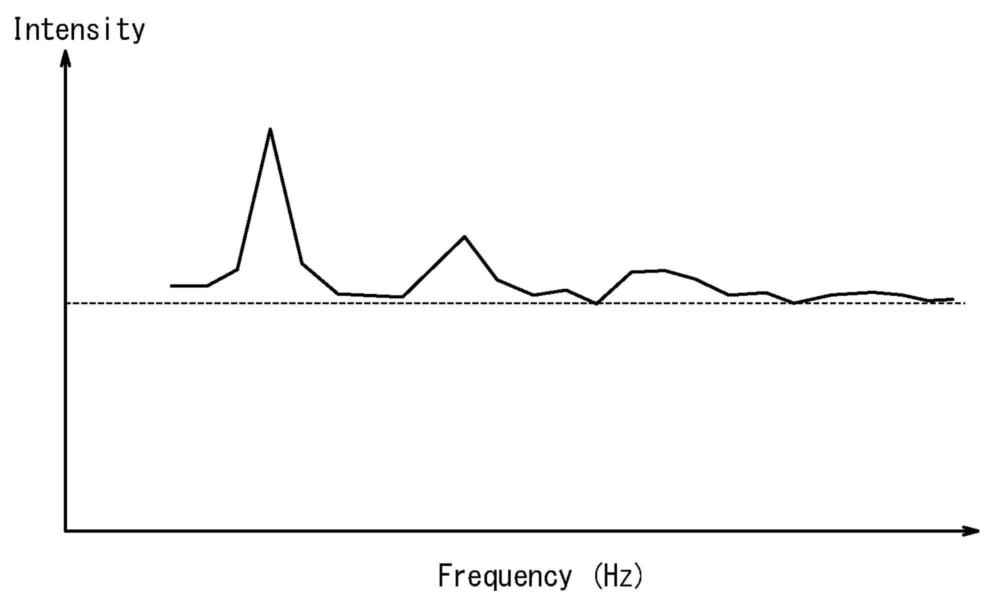
FIG. 13B illustrates the result of performing a fast Fourier transform (FFT) on the pulse wave of FIG. 13A.

FIG. 13A illustrates a pulse wave for explaining another example of an estimation method based on change in the pulse wave. FIG. 13B illustrates the result of performing a fast Fourier transform (FFT) on the pulse wave of FIG. 13A. The estimation formulas for estimating the blood glucose level are, for example, derived by regression analysis related to a fundamental and harmonic component (Fourier coefficients) that are derived by the FFT. The peak value in the result of the FFT illustrated in FIG. 13B changes in accordance with change in pulse wave. Therefore, the blood glucose level can be estimated with estimation formulas derived using the Fourier coefficients.

The above-described rising index SI, the AI, and the pulse rate PR, along with coefficients related to pulse wave characteristics used to derive the estimation formula by regression analysis, such as the Fourier coefficient and the like, are referred to as characteristic coefficients in this disclosure. The electronic device 100 uses estimation formulas based on the characteristic coefficients of a pulse wave as the pulse wave index to estimate the subject's glucose metabolism.

Here, a method for deriving the estimation formulas for the case of the electronic device 100 estimating the subject's glucose metabolism in accordance with characteristic coefficients of a pulse wave is described. Here, an example of using the Fourier coefficients as characteristic coefficients is described. The estimation formulas need not be derived by the electronic device 100 and may be derived in advance using another computer. In this disclosure, the device that derives the estimation formulas is referred to as an estimation formula derivation apparatus. The derived estimation formulas are, for example, stored in the memory 145 in advance, before the subject estimates the blood glucose level with the electronic device 100.

Figure 14:
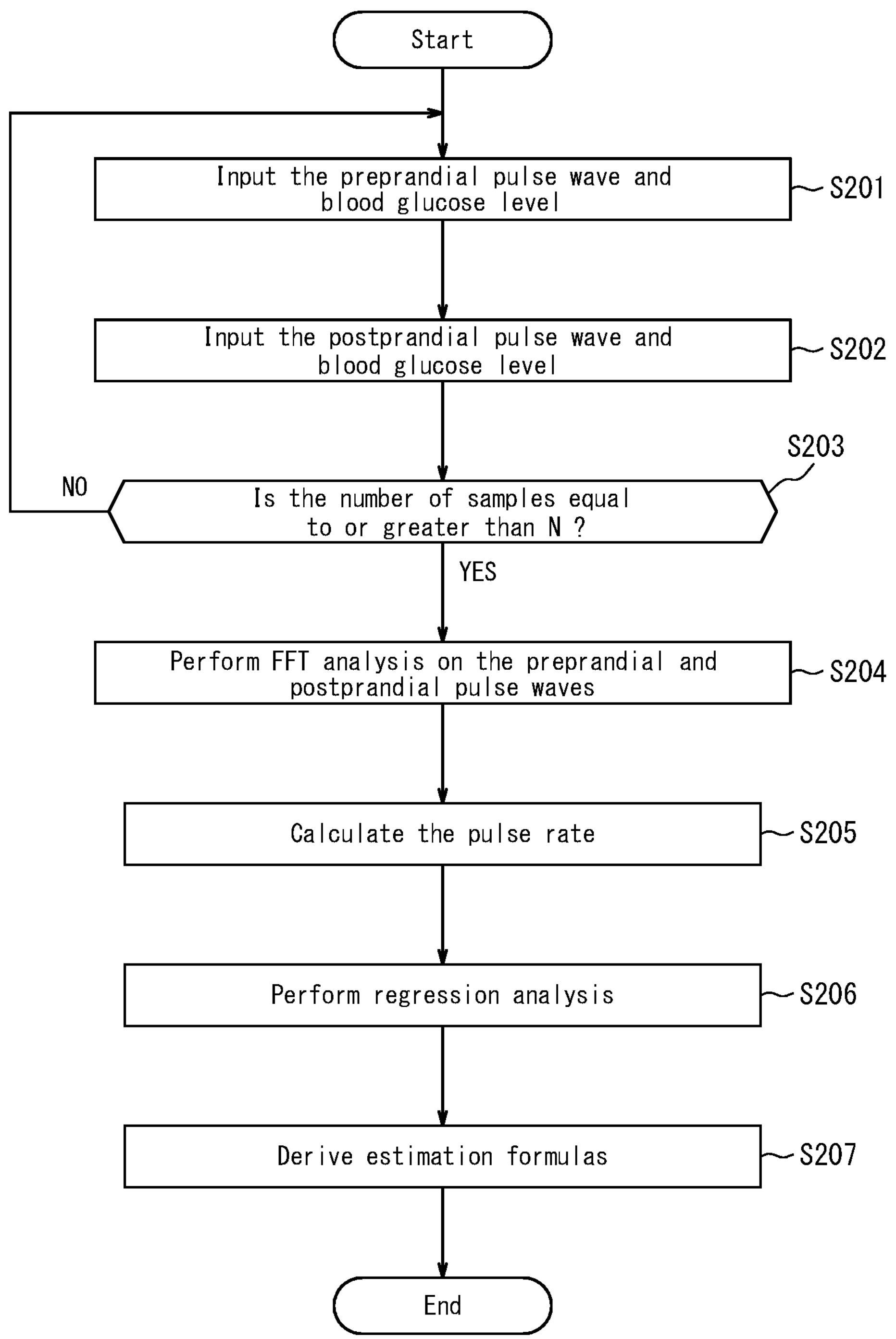
FIG. 14 is a flowchart for creating estimation formulas used by the electronic device according to Embodiment 2 of this disclosure.

FIG. 14 is a flowchart for deriving the estimation formulas used by the electronic device 100 according to this embodiment. The estimation formulas are derived by performing regression analysis based on the sample data obtained by measuring a subject's preprandial and postprandial pulse wave and blood glucose level using a pulse wave meter and a blood glucose meter respectively. In this context, preprandial refers to when the subject is fasting, and postprandial refers to the time when the blood glucose level rises after a predetermined length of time elapses after a meal (for example, approximately one hour after the start of the meal). The definitions of preprandial and postprandial are the same hereafter in this disclosure. The acquired sample data are not limited to before and after a meal. It suffices to use data for time slots with large variation in the blood glucose level.

First, during derivation of the estimation formulas, information on the subject's preprandial pulse wave and blood glucose level, as measured respectively by a pulse wave meter and a blood glucose meter, is input into the estimation formula derivation apparatus (step S201).

Information on the subject's postprandial pulse wave and blood glucose level, as measured respectively by a pulse wave meter and a blood glucose meter, is also input into the estimation formula derivation apparatus (step S202).

The estimation formula derivation apparatus determines whether the number of samples in the sample data input in step S201 and step S202 is equal to or greater than the number of samples, N, sufficient for regression analysis (step S203). When it is determined that the number of samples is fewer than N (NO), the estimation formula derivation apparatus repeats step S201 and step S202 until the number of samples becomes equal to or greater than N. Conversely, when it is determined that the number of samples is greater than or equal to N (YES), the estimation formula derivation apparatus proceeds to step S204 and calculates the estimation formulas.

During calculation of the estimation formulas, the estimation formula derivation apparatus performs FFT analysis on the input preprandial and postprandial pulse waves (step S204). Based on the FFT analysis, the estimation formula apparatus extracts the fundamental and harmonic components corresponding to the Fourier coefficients.

The estimation formula derivation apparatus also calculates the pulse rate of each subject on the basis of the input pulse waves (step S205).

The estimation formula derivation apparatus then performs regression analysis (step S206). The regression analysis may be performed with any suitable method, such as partial least squares regression. The dependent variable in the regression analysis is the blood glucose level, including the preprandial and postprandial blood glucose level. The explanatory variable in the regression analysis is calculated in accordance with the preprandial and postprandial Fourier coefficients (fundamental and harmonic components) and pulse rate. In greater detail, the estimation formula derivation apparatus standardizes the fundamental and harmonic components and multiplies by the pulse rate to calculate the explanatory variable.

The estimation formula derivation apparatus derives estimation formulas for estimating the blood glucose level on the basis of the result of regression analysis (step S207). An example of estimation formulas for estimating the blood glucose level is indicated below by Formula (1) and Formula (2).

$$GLa=-26.9+PRb\times(-1.61\times Sb_1+0.59\times Sb_2+2.89\times Sb_3+4.31\times Sb_4-1.66\times Sb_5)+PRa\times(2.86\times Sa_1-1.2\times Sa_2-2.14\times Sa_3-1.4\times Sa_4+11.29\times Sa_5) \quad (1)$$

$$GLb=91.2+PRb\times(-0.36\times Sb_1+0.42\times Sb_2+0.31\times Sb_3-0.28\times Sb_4+1.67\times Sb_5)+PRa\times(0.49\times Sa_1-0.29\times Sa_2-0.14\times Sa_3-1.23\times Sa_4-0.21\times Sa_5) \quad (2)$$

In Formulas (1) and (2), GLa is the postprandial blood glucose level, and GLb is the preprandial blood glucose level. PRa is the postprandial pulse rate, and PRb is the preprandial pulse rate. $Sb_1$ to $Sb_5$ are first order to fifth order Fourier coefficients obtained by a FFT analysis of the preprandial pulse wave. $Sa_1$ to $Sa_5$ are first order to fifth order Fourier coefficients obtained by a FFT analysis of the postprandial pulse wave.

An example of calculating the explanatory variable on the basis of the Fourier coefficients and the pulse rate has been described with reference to FIG. 14, but the explanatory variable is not limited to this example. For example, the explanatory variable may be calculated on the basis of the subject's age, the rising index SI, the AI, the pulse rate PR, and the like. In this case, the subject's age, the rising index SI, the AI, the pulse rate PR, and the like are input in step S201 and step S202 of FIG. 14.

Figure 15:
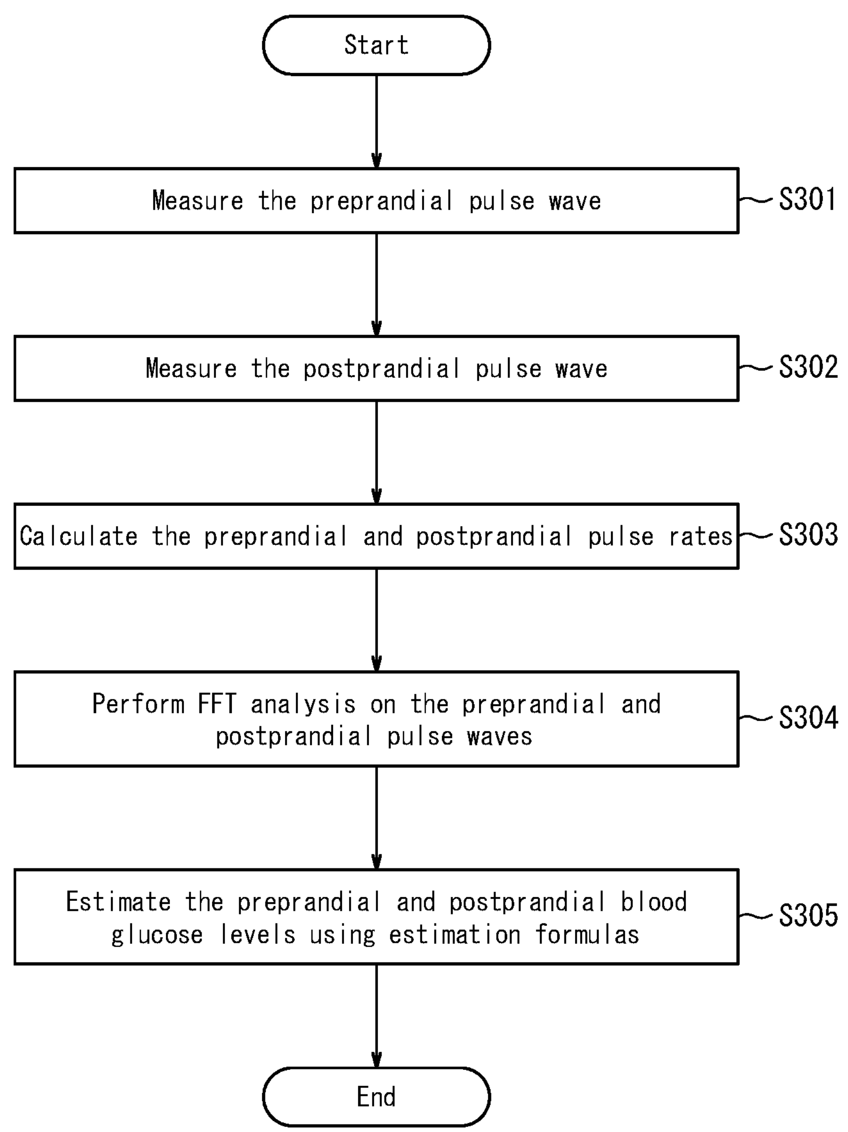
FIG. 15 is a flowchart for estimating a subject's blood glucose level using the estimation formulas derived using the flow in FIG. 14.

Next, a process for estimating the subject's blood glucose level using estimation formulas is described. FIG. 15 is a flowchart for estimating a subject's blood glucose level using the estimation formulas derived according to the flow illustrated in FIG. 14.

First, the electronic device 100 measures the subject's preprandial pulse wave in response to operation by the subject (step S301).

After the subject eats a meal, the electronic device 100 also measures the subject's postprandial pulse wave in response to operation by the subject (step S302).

The electronic device 100 then calculates the subject's preprandial and postprandial pulse rate on the basis of the measured pulse wave (step S303).

The electronic device 100 performs FFT analysis on the subject's preprandial and postprandial pulse wave on the basis of the measured pulse wave (step S304). The electronic device 100 calculates the characteristic coefficients based on the FFT analysis.

The electronic device 100 estimates the subject's preprandial and postprandial blood glucose level by, for example, substituting the characteristic coefficients calculated in step S304 into Formula (1) and Formula (2) above (step S305). The subject is notified, for example, of the estimated blood glucose level by the notification interface 147 of the electronic device 100.

During derivation of the estimation formulas in FIG. 14, when the explanatory variable is calculated on the basis of the subject's age, the rising index SI, the AI, the pulse rate PR, and the like, then in step S204 of the flowchart in FIG. 14, the electronic device 100 calculates the rising index SI, the AI, the pulse rate PR, and the like on the basis of the measured pulse. In step S305, the electronic device 100 then estimates the subject's blood glucose level using the estimation formulas based on the calculated rising index SI, the AI, the pulse rate PR, and the like.

Figure 16:
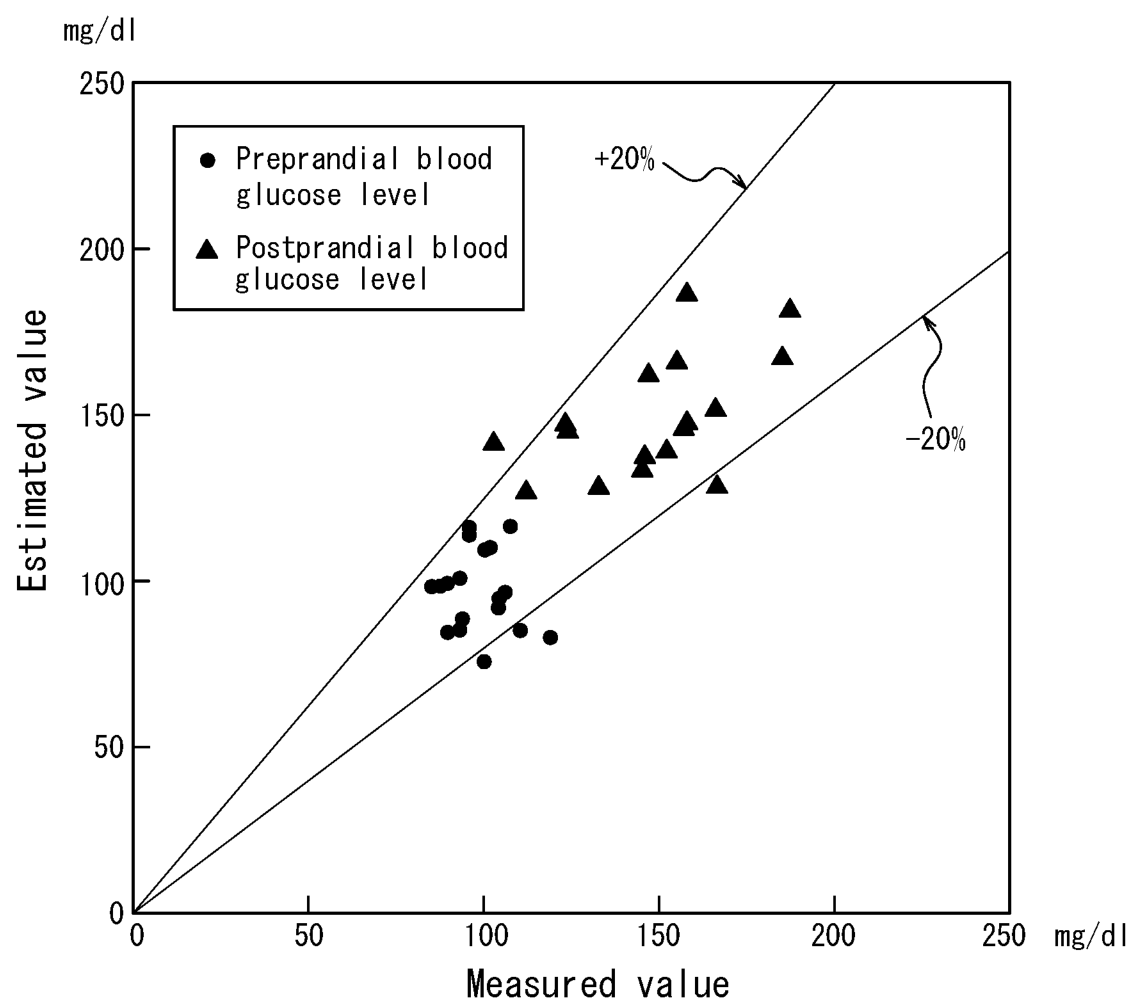
FIG. 16 illustrates a comparison between the blood glucose level estimated using the estimation formulas derived using the flow in FIG. 14 and the actual measured blood glucose level.

FIG. 16 illustrates a comparison between the blood glucose level estimated using the estimation formulas derived using the flow in FIG. 14 and the actual measured blood glucose level. In the graph in FIG. 16, the measured value of the blood glucose level (actual measured value) is indicated on the horizontal axis, and the estimated value of the blood glucose level is indicated on the vertical axis. As illustrated in FIG. 16, the measured values and the estimated values are mostly contained within a range of ±20%. In other words, the estimation accuracy with the estimation formulas is considered to be within 20%.

In this way, the electronic device 100 can estimate the subject's glucose metabolism in a non-invasive manner and in a short time.

Embodiment 3

According to Embodiment 2, an example of deriving estimation formulas by performing regression analysis on the basis of sample data for preprandial and postprandial blood glucose level and pulse wave was described. In Embodiment 3, an example of deriving estimation formulas on the basis of sample data for preprandial and postprandial blood glucose level and postprandial pulse wave is described. Description of points that are similar to those of Embodiment 2 is omitted as appropriate.

Figure 17:
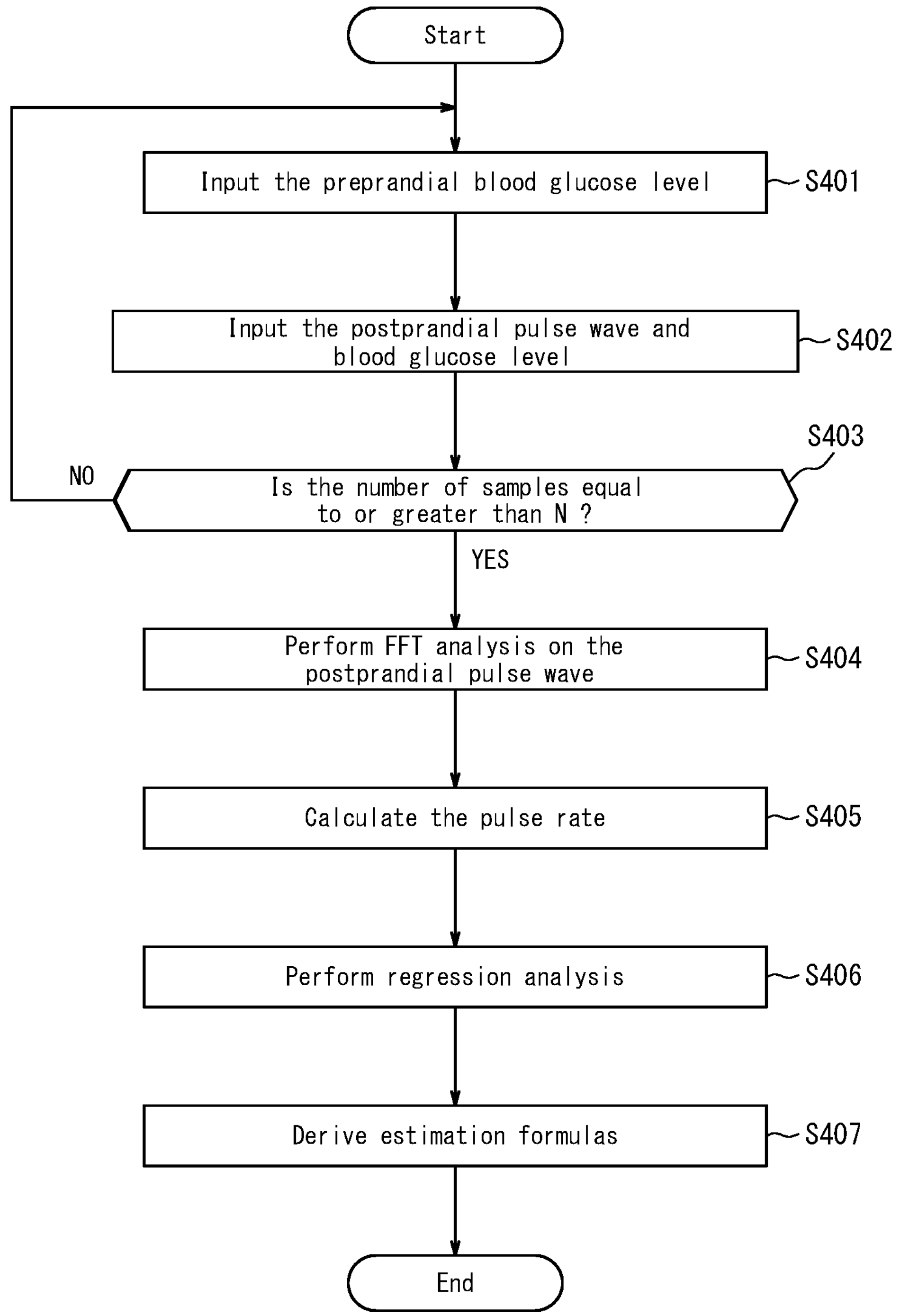
FIG. 17 is a flowchart for creating estimation formulas used by an electronic device according to Embodiment 3 of this disclosure.

FIG. 17 is a flowchart for deriving estimation formulas used by an electronic device 100 according to this embodiment. The estimation formulas are derived by performing regression analysis on the basis of sample data obtained by measuring a subject's postprandial pulse wave using a pulse wave meter and measuring the subject's preprandial and postprandial blood glucose level using a blood glucose meter.

During derivation of the estimation formulas according to this embodiment, information on the subject's preprandial blood glucose level, as measured by a blood glucose meter, is input into the estimation formula derivation apparatus (step S401). Step S402 and step S403 are similar to step S202 and step S203 respectively of FIG. 14.

When it is determined that the number of samples is equal to or greater than N (YES), the estimation formula derivation apparatus performs FFT analysis on the input postprandial pulse wave (step S404). Based on the FFT analysis, the estimation formula derivation apparatus extracts the fundamental and harmonic components corresponding to the Fourier coefficients.

The estimation formula derivation apparatus also calculates the pulse rate of each subject on the basis of the input pulse wave (step S405).

The estimation formula derivation apparatus then performs regression analysis (step S406). The dependent variable in the regression analysis in this embodiment is the blood glucose level, including the preprandial and postprandial blood glucose level. The explanatory variable in the regression analysis in this embodiment is calculated on the basis of the postprandial Fourier coefficients (fundamental and harmonic components) and pulse rate.

The estimation formula derivation apparatus derives estimation formulas for estimating the blood glucose level on the basis of the result of regression analysis (step S407). An example of estimation formulas for estimating the blood glucose level as derived using the flow illustrated in FIG. 17 is indicated below by Formula (3) and Formula (4).

$$GLa=-39.7+PRa\times(2.38\times Sa_1-0.91\times Sa_2-1.27\times Sa_3-3.7\times Sa_4+6.22\times Sa_5) \quad (3)$$

$$GLb=81.4+PRa\times(0.22\times Sa_1-0.22\times Sa_2-0.2\times Sa_3-1.66\times Sa_4+2.27\times Sa_5) \quad (4)$$

Figure 18:
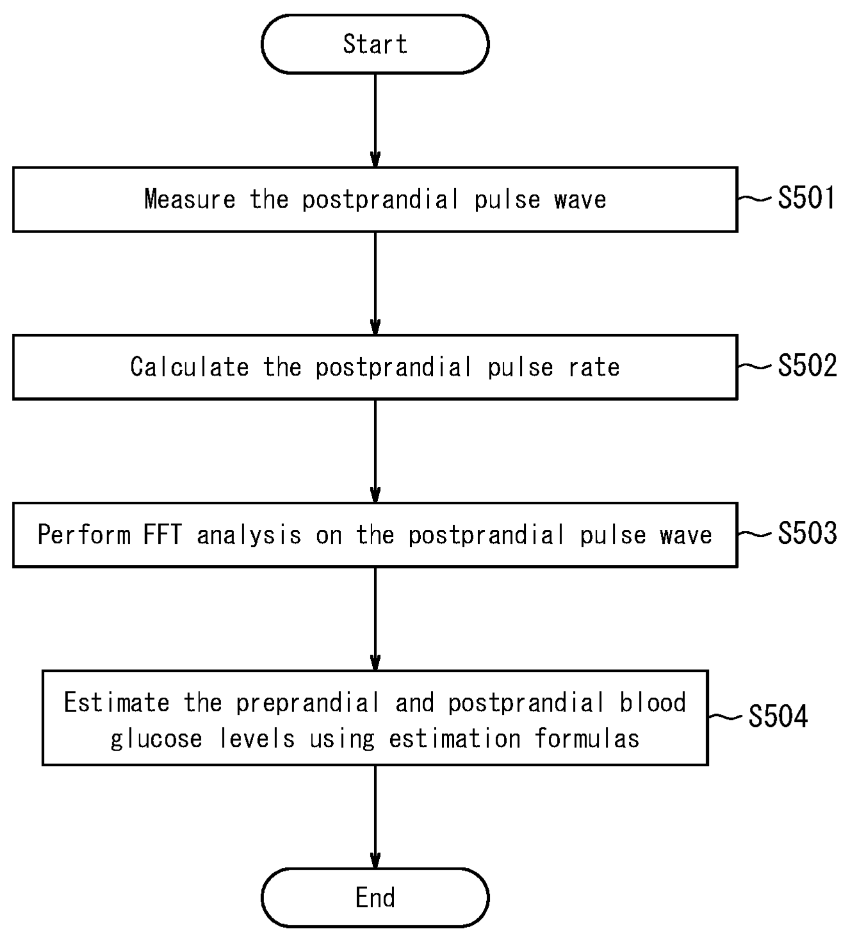
FIG. 18 is a flowchart for estimating a subject's blood glucose level using the estimation formulas derived using the flow in FIG. 17.

Next, the process for estimating the subject's blood glucose level using estimation formulas is described. FIG. 18 is a flowchart for estimating a subject's blood glucose level using the estimation formulas derived using the flow illustrated in FIG. 17.

After the subject eats a meal, the electronic device 100 measures the subject's postprandial pulse wave in response to operation by the subject (step S501).

The electronic device 100 calculates the subject's preprandial and postprandial pulse rate on the basis of the measured pulse wave (step S502).

The electronic device 100 performs FFT analysis on the subject's postprandial pulse wave on the basis of the measured pulse wave (step S503). The electronic device 100 calculates the characteristic coefficients based on the FFT analysis.

The electronic device 100 estimates the subject's preprandial and postprandial blood glucose level by, for example, substituting the characteristic coefficients calculated in step S503 into Formula (3) and Formula (4) above (step S504). The subject is notified, for example, of the estimated blood glucose level by the notification interface 147 of the electronic device 100.

Figure 19:
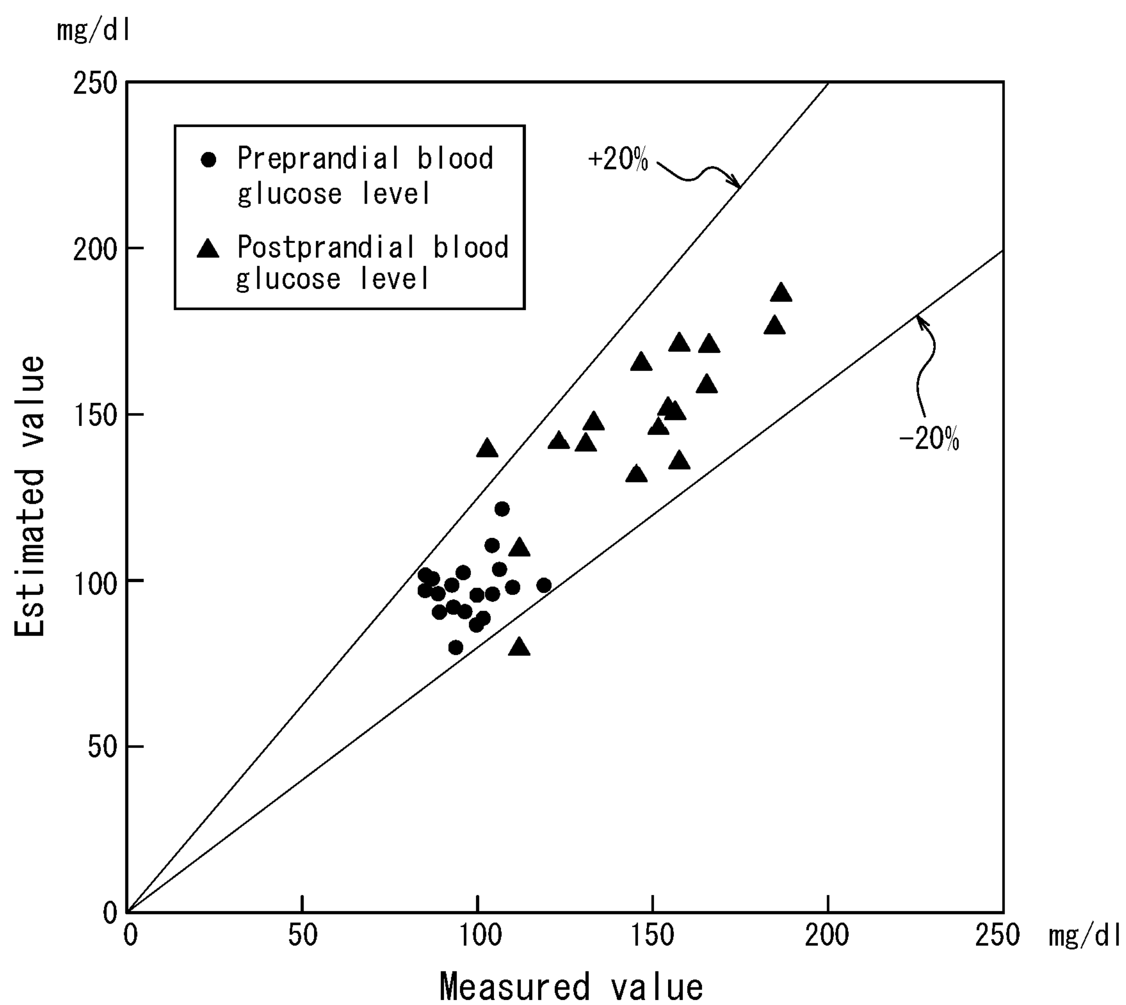
FIG. 19 illustrates a comparison between the blood glucose level estimated using the estimation formulas derived using the flow in FIG. 17 and the actual measured blood glucose level.

FIG. 19 illustrates a comparison between the blood glucose level estimated using the estimation formulas derived using the flow in FIG. 17 and the actual measured blood glucose level. In the graph in FIG. 19, the measured value of the blood glucose level (actual measured value) is indicated on the horizontal axis, and the estimated value of the blood glucose level is indicated on the vertical axis. As illustrated in FIG. 19, in this embodiment as well, the measured values and the estimated values are mostly contained within a range of ±20%. In other words, the estimation accuracy with the estimation formulas is considered to be within 20%.

In this way, if sample data for which regression analysis is possible can be acquired, the electronic device 100 can estimate the subject's glucose metabolism in a non-invasive manner and in a short time using the estimation formulas, even in cases where the estimation formulas are derived on the basis of the postprandial pulse wave.

Embodiment 4

According to Embodiments 2 and 3, examples of the electronic device 100 estimating the subject's blood glucose level (glucose metabolism) have been described. In Embodiment 4, an example of the electronic device 100 estimating the subject's lipid metabolism is described. In this embodiment, the electronic device 100 estimates the lipid level as the subject's lipid metabolism. Here, the lipid level includes neutral lipids, total cholesterol, HDL cholesterol, LDL cholesterol, and the like. In the description of this embodiment, description of points that are similar to Embodiment 2 is omitted as appropriate.

The electronic device 100 stores estimation formulas for estimating the lipid level on the basis of the pulse wave in the memory 145, for example, in advance. The electronic device 100 estimates the lipid level using these estimation formulas.

The estimation theory related to estimating the lipid level on the basis of a pulse wave is similar to the estimation theory for blood glucose level described in Embodiment 2. In other words, unlike the preprandial lipid level in the blood, a change in the postprandial lipid level in the blood is also reflected in a change in the pulse wave. Therefore, the electronic device 100 can acquire the pulse wave and estimate the lipid level based on the change in the acquired pulse wave.

Estimation formulas for estimating the lipid level can be derived by performing regression analysis on sample data representing preprandial lipid levels and pulse waves obtained from a plurality of subjects. By applying the derived estimation formulas to the index based on the subject's pulse wave at the time of estimation, the subject's lipid level can be estimated.

Figure 20:
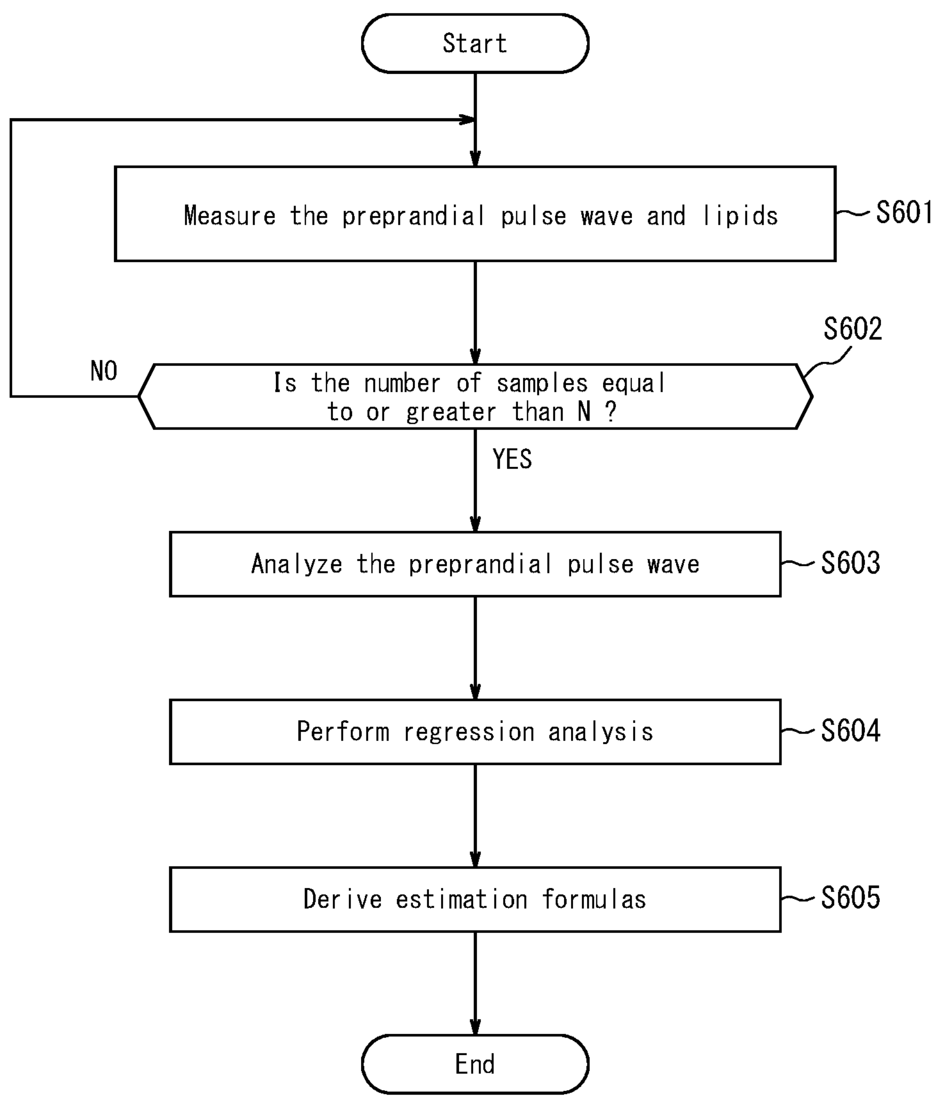
FIG. 20 is a flowchart for creating estimation formulas used by an electronic device according to Embodiment 4 of this disclosure.

FIG. 20 is a flowchart for deriving estimation formulas used by the electronic device 100 according to Embodiment 4. The estimation formulas are derived by performing regression analysis on the basis of sample data obtained by measuring the preprandial pulse wave of a subject using a pulse wave meter and measuring the preprandial lipid level of the subject using a lipid measurement apparatus.

During derivation of the estimation formulas, first, information on the preprandial pulse wave and lipid level of the subject, as measured respectively by a pulse wave meter and a lipid measurement apparatus, is input into the estimation formula derivation apparatus (step S601). At this time, the age of the subject is also input.

The estimation formula derivation apparatus determines whether the number of samples in the sample data input in step S601 is equal to or greater than the number of samples, N, sufficient for regression analysis (step S602). When it is determined that the number of samples is fewer than N (NO), the estimation formula derivation apparatus repeats step S601 until the number of samples becomes equal to or greater than N. Conversely, when it is determined that the number of samples is greater than or equal to N (YES), the estimation formula derivation apparatus proceeds to step S603 and calculates the estimation formulas.

During calculation of the estimation formulas, the estimation formula derivation apparatus analyzes the input preprandial pulse wave (step S603). For example, in greater detail, the estimation formula derivation apparatus analyzes the rising index SI, the AI, and/or the pulse rate PR of the pulse wave.

The estimation formula derivation apparatus then performs regression analysis (step S604). The objective variable in the regression analysis is the preprandial lipid level. The explanatory variables in the regression analysis are, for example, the age input in step S601 and the rising index SI, the AI, and/or the pulse rate PR of the preprandial pulse wave analyzed in step S603. The explanatory variables may, for example, also be Fourier coefficients calculated as the result of an FFT analysis.

The estimation formula derivation apparatus derives estimation formulas for estimating the lipid level on the basis of the result of regression analysis (step S605). An example of estimation formulas for estimating the lipid level is indicated below by Formulas (5) through (8).

$$\mathrm{HDL}=-14.5+0.14\times \mathrm{age}-0.37\times PR+0.07\times AI-0.42\times SI \quad (5)$$

$$\mathrm{LDL}=-241.4+0.34\times \mathrm{age}+0.79\times PR+3.18\times AI-1.69\times SI \quad (6)$$

$$\mathrm{Chol}=-185.1+1.01\times \mathrm{age}+0.35\times PR+2.41\times AI-2.01\times SI \quad (7)$$

$$Tg=383+2.53\times \mathrm{age}-0.27\times PR-4.59\times AI+0.67\times SI \quad (8)$$

In Formulas (5) through (8), HDL represents HDL cholesterol, LDL represents LDL cholesterol, Chol represents total cholesterol, and Tg represents the numerical value of neutral lipids. Also, age indicates the age of the subject.

Figure 21:
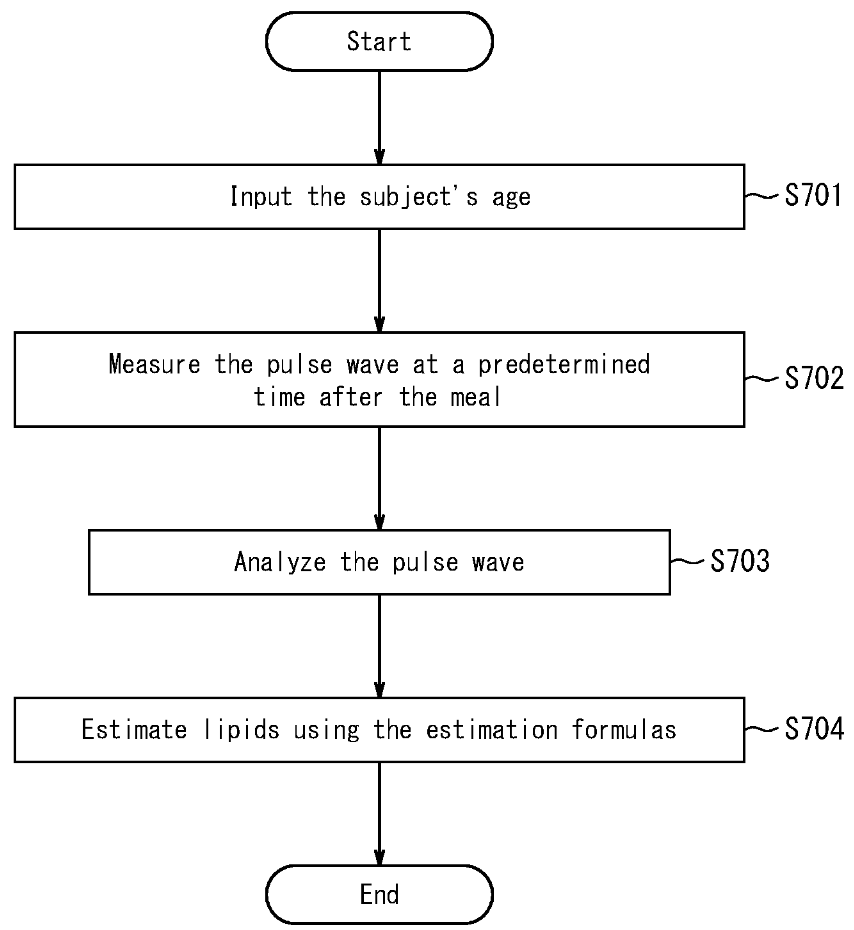
FIG. 21 is a flowchart for estimating a subject's lipid level using the estimation formulas derived using the flow in FIG. 20.

Next, a process for estimating the lipid level of the subject using estimation formulas is described. FIG. 21 is a flowchart for estimating a subject's lipid level using the estimation formulas derived using the flow in FIG. 20.

First, the age of the subject is input to the electronic device 100 in response to an operation by the subject (step S701).

After the subject eats a meal, the electronic device 100 also measures, at a predetermined time, the postprandial pulse wave of the subject, in response to an operation by the subject (step S702). Here, the predetermined time after the meal is any time at which the change in lipid level due to a meal is reflected in a change in pulse wave. The predetermined time after the meal may be a time excluding the time immediately after completion of the meal, at which the blood glucose level rises.

The electronic device 100 then analyzes the measured pulse wave (step S703). For example, in greater detail, the electronic device 100 analyzes the rising index SI, the AI, and/or the pulse rate PR related to the measured pulse wave.

The electronic device 100 estimates the subject's lipid level by, for example, substituting the rising index SI, the AI, and/or the pulse rate PR analyzed in step S703 and the age of the subject into Formulas (5) through (8) above (step S704). The subject is notified, for example, of the estimated lipid level by the notification interface 147 of the electronic device 100.

Figure 22:
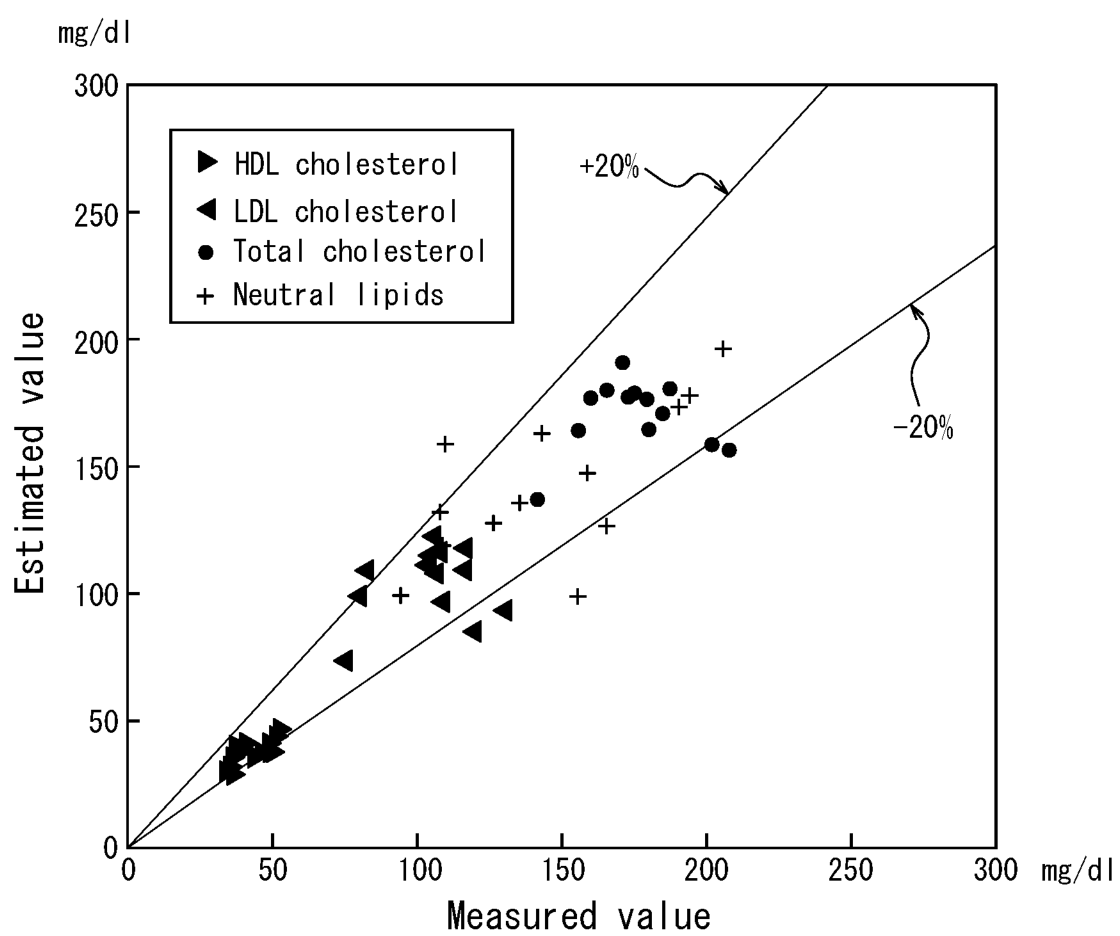
FIG. 22 illustrates a comparison between the lipid level estimated using the estimation formulas derived using the flow in FIG. 20 and the actual measured lipid level.

FIG. 22 illustrates a comparison between the lipid level estimated using the estimation formulas derived using the flow in FIG. 20 and the actual measured lipid level. In the graph in FIG. 22, the measured value of the lipid level (actual measured value) is indicated on the horizontal axis, and the estimated value of the lipid level is indicated on the vertical axis. The measured value of each type of lipid level was measured with a "cobas b101" manufactured by Roche Diagnostics. As illustrated in FIG. 22, the measured values and the estimated values are mostly contained within a range of ±20%. In other words, the estimation accuracy with the estimation formulas is considered to be within 20%.

In this way, the electronic device 100 can estimate the subject's lipid metabolism in a non-invasive manner and in a short time.

Figure 23:
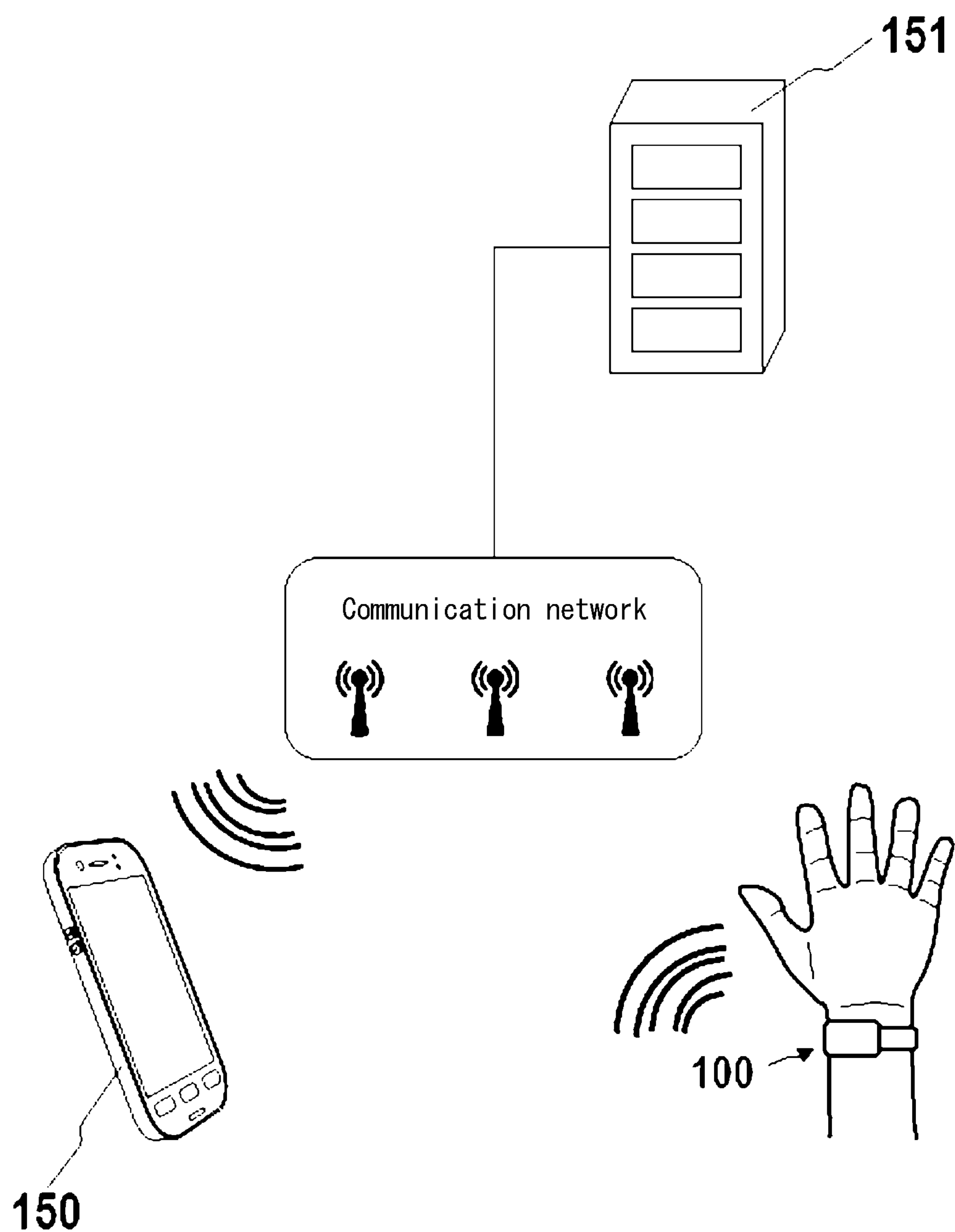
FIG. 23 illustrates the configuration of a system according to an embodiment of this disclosure.

FIG. 23 illustrates the configuration of a system according to an embodiment of this disclosure. The system according to the embodiment illustrated in FIG. 23 includes an electronic device 100, a server 151, a mobile terminal 150, and a communication network. As illustrated in FIG. 23, the pulse wave index calculated by the electronic device 100 is transmitted to the server 151 through the communication network and is stored on the server 151 as the subject's personal information. In the server 151, the fluidity of the subject's blood and the state of the subject's glucose metabolism and lipid metabolism are estimated by comparison with the subject's past acquired information and with a variety of databases. The server 151 further creates appropriate advice for the subject. The server 151 replies to the mobile terminal 150 in the subject's possession with estimation results and advice. The mobile terminal 150 can establish a system to provide notification, via the display of the mobile terminal 150, of the received estimation results and advice. By using the communication capability of the electronic device 100, information from a plurality of users can be collected on the server 151, thereby further improving the estimation accuracy. Furthermore, since the mobile terminal 150 is used as notification means, the electronic device does not require the notification interface 147 and can be further reduced in size. Since the fluidity of the subject's blood and the state of the subject's glucose metabolism and lipid metabolism are estimated by the server 151, the calculation load on the controller 143 of the electronic device 100 can be reduced. Furthermore, the subject's past acquired information can be stored on the server 151, thereby reducing usage of the memory 145 of the electronic device 100. Therefore, the electronic device 100 can be further reduced in size and complexity. The processing speed for calculation is also improved.

In the system according to this embodiment, the electronic device 100 and the mobile terminal 150 have been illustrated as connected over the communication network via the server 151. However, systems according to this disclosure are not limited to this configuration. The electronic device 100 and the mobile terminal 150 may be connected directly over the communication network without use of the server 151.

Characteristic embodiments have been described for a complete and clear disclosure. The appended claims, however, are not limited to the above embodiments and are to be construed as encompassing all of the possible modifications and alternate configurations that a person of ordinary skill in the art could make within the scope of the fundamental features indicated in this disclosure.

For example, in the above embodiments, cases where the sensor 130 is provided with the angular velocity sensor 131 has been described, but the electronic device 100 according to this disclosure is not limited to this case. The sensor 130 may be provided with an optical pulse wave sensor constituted by an optical emitter and an optical detector or may be provided with a pressure sensor. Furthermore, the electronic device 100 is not limited to being worn on the wrist. It suffices for the sensor 130 to be placed on an artery, such as on the neck, ankle, thigh, ear, or the like.

For example, in Embodiment 1, the state of glucose metabolism and lipid metabolism of a subject is estimated using a first extreme value and second extreme value of a pulse wave index and the times thereof, but an electronic device according to this disclosure is not limited to this case. In some cases, only one extreme value or no extreme value may be observed, and the state of glucose metabolism and lipid metabolism of the subject may be estimated on the basis of the overall trend (for example, integral value, Fourier transform, or the like) in the temporal change in the calculated pulse wave index. Furthermore, instead of extracting the extreme values of the pulse wave index, the state of glycolipid metabolism of the subject may be estimated on the basis of a time range over which the pulse wave index becomes equal to or less than a predetermined.

For example, in the above embodiments, cases where estimation of preprandial and postprandial fluidity of blood has been described, but the electronic device 100 according to this disclosure is not limited to these cases. The electronic device according to this disclosure may estimate blood fluidity before or after exercise and during exercise, or may estimate the blood fluidity before or after bathing and during bathing.

REFERENCE SIGNS LIST

100 Electronic device
110 Wearing portion
120 Measurement unit
120*a* Back face
120*b* Front face
111 Opening
130 Sensor
131 Angular velocity sensor
132 Pulse pad
133 Support
140 Elastic body
143 Controller
144 Power source
145 Memory
146 Communication interface
147 Notification interface
150 Mobile terminal
151 Server

The invention claimed is:

1. An electronic device comprising:
a sensor configured to acquire a pulse wave; and
a controller configured to calculate an index based on a feature of a reflected wave of the acquired pulse wave, the feature of the reflected wave including at least one of,
a magnitude of the reflected wave,
a time difference between the acquired pulse wave and the reflected wave, or
an augmentation index based on a ratio between a magnitude of the acquired pulse wave and a magnitude of the reflected wave, wherein
the controller estimates a state of glucose metabolism or lipid metabolism of a subject using the calculated index.

2. The electronic device of claim 1, wherein as the index based on the acquired pulse wave, the controller calculates at least one of pulse wave velocity or posterior systolic blood pressure using the acquired pulse wave and estimates the state of glucose metabolism or lipid metabolism of the subject.

3. The electronic device of claim 1, wherein as the index based on the acquired pulse wave, the controller calculates a characteristic coefficient of the acquired pulse wave and estimates the state of glucose metabolism or lipid metabolism of the subject.

4. The electronic device of claim 1, wherein the controller estimates a blood glucose level as the glucose metabolism of the subject or estimates a lipid level as the lipid metabolism of the subject.

5. The electronic device of claim 1, wherein
the sensor acquires pulse waves at a plurality of times, and
the controller calculates a plurality of indices corresponding to the pulse waves acquired at the plurality of times and estimates the state of glucose metabolism or lipid metabolism of the subject in accordance with change over time of the calculated indices.

6. The electronic device of claim 5, wherein the sensor acquires the pulse waves at the plurality of times, and the plurality of times includes at least before a meal and after a meal.

7. The electronic device of claim 6, wherein the controller extracts extreme values from the index for after the meal and estimates the state of glucose metabolism of the subject in accordance with a first extreme value occurring earliest within a predetermined length of time after the meal and an occurrence time of the first extreme value.

8. The electronic device of claim 6, wherein the controller extracts extreme values from the index for after the meal and estimates the state of lipid metabolism of the subject in accordance with a second extreme value occurring after a predetermined length of time elapses after the meal and an occurrence time of the second extreme value.

9. The electronic device of claim 6, wherein the controller extracts extreme values from the index for after the meal, estimates the state of glucose metabolism of the subject in accordance with a first extreme value occurring earliest after the meal and an occurrence time of the first extreme value, and estimates the state of lipid metabolism of the subject in accordance with a second extreme value occurring after the first extreme value and an occurrence time of the second extreme value.

10. An electronic device comprising:
a sensor configured to acquire a pulse wave; and
a controller configured to calculate an index based on a feature of a reflected wave of the acquired pulse wave, the feature of the reflected wave including at least one of,
a magnitude of the reflected wave,
a time difference between the acquired pulse wave and the reflected wave, or
an augmentation index based on a ratio between a magnitude of the acquired pulse wave and a magnitude of the reflected wave, wherein
the controller estimates the blood fluidity of a subject using the calculated index.

11. The electronic device of claim 1, wherein the sensor comprises at least an acceleration sensor configured to detect acceleration or an angular velocity sensor configured to detect angular velocity.

12. A system comprising:
a terminal comprising a sensor configured to acquire a pulse wave;
a device configured to estimate a state of glucose metabolism or lipid metabolism of a subject using a feature of a reflected wave of the acquired pulse wave, the feature of the reflected wave including at least one of,
a magnitude of the reflected wave,
a time difference between the acquired pulse wave and the reflected wave, or an augmentation index based on a ratio between a magnitude of the acquired pulse wave and a magnitude of the reflected wave; and a notification apparatus configured to notify the subject of the estimated state of glucose metabolism or lipid metabolism.

* * * * *